(12) United States Patent
Zumeris et al.

(10) Patent No.: US 7,431,892 B2
(45) Date of Patent: Oct. 7, 2008

(54) APPARATUS FOR STERILIZING A LIQUID WITH FOCUSED ACOUSTIC STANDING WAVES

(75) Inventors: Jona Zumeris, Nesher (IL); Jacob Levy, Haifa (IL); Zadik Hazan, Ganei Yehuda (IL); Yanina Zumeris, Nesher (IL)

(73) Assignee: Piezo Top Ltd., Haifa (IL)

( * ) Notice: Subject to any disclaimer, the term of this patent is extended or adjusted under 35 U.S.C. 154(b) by 673 days.

(21) Appl. No.: 10/254,014

(22) Filed: Sep. 25, 2002

(65) Prior Publication Data

US 2004/0057866 A1    Mar. 25, 2004

Related U.S. Application Data

(60) Provisional application No. 60/324,281, filed on Sep. 25, 2001.

(51) Int. Cl.
    *C02F 1/36* (2006.01)
(52) U.S. Cl. .................... 422/128; 366/114; 366/127
(58) Field of Classification Search ................. 210/748; 422/20, 128; 366/114, 115, 127, 322; 310/322
    See application file for complete search history.

(56) References Cited

U.S. PATENT DOCUMENTS

| | | | |
|---|---|---|---|
| 3,230,137 A | 1/1966 | Ellison | |
| 3,254,284 A * | 5/1966 | Tomes | ........................ 318/118 |
| 3,464,672 A | 9/1969 | Massa | |
| 3,634,025 A | 1/1972 | Landry | |
| 3,700,406 A | 10/1972 | Landry | |
| 3,837,800 A | 9/1974 | Wood | |
| 3,889,123 A | 6/1975 | Bosshard | |
| 3,894,236 A | 7/1975 | Hazelrigg | |
| 4,003,832 A | 1/1977 | Henderson et al. | |
| 4,308,229 A | 12/1981 | Voit | |
| 4,433,399 A | 2/1984 | Massa et al. | |
| 4,471,225 A | 9/1984 | Hillman | |
| 4,597,876 A | 7/1986 | Hall | |
| 4,602,162 A | 7/1986 | Sperry, III et al. | |
| 4,691,724 A | 9/1987 | Garcia et al. | |
| 4,728,368 A | 3/1988 | Pedziwiatr | |
| 5,305,737 A | 4/1994 | Vago | |
| 5,997,812 A | 12/1999 | Burnham et al. | |

(Continued)

FOREIGN PATENT DOCUMENTS

DE    19517381    7/1996

(Continued)

OTHER PUBLICATIONS

Microbiological Examination Report Standard Methods for the Examination of water and waste water. AminoLab Laboratory Jan. 2001. (as cited in the application).

(Continued)

*Primary Examiner*—Matthew O Savage
(74) *Attorney, Agent, or Firm*—Pearl Cohen Zedek Latzer, LLP

(57) ABSTRACT

Apparatus and method for sterilization of liquid includes a liquid container containing a liquid and having a piezoceramic ring that is connected to a power supply system. Power supply system supplies electric signals to the piezoceramic ring that are transformed into mechanical waves and cause vibrations in the liquid.

15 Claims, 35 Drawing Sheets

U.S. PATENT DOCUMENTS

| | | | |
|---|---|---|---|
| 6,019,947 A | 2/2000 | Kucherov | |
| 6,071,473 A | 6/2000 | Darwin | |
| 6,605,252 B2 * | 8/2003 | Omasa | 422/20 |
| 6,770,248 B2 * | 8/2004 | Haggett et al. | 422/128 |
| 6,916,418 B2 * | 7/2005 | Baldasarre et al. | 210/205 |

FOREIGN PATENT DOCUMENTS

| | | |
|---|---|---|
| DE | 19844310 | 3/2000 |

OTHER PUBLICATIONS

International Search Report PCT/IL02/00789.

\* cited by examiner

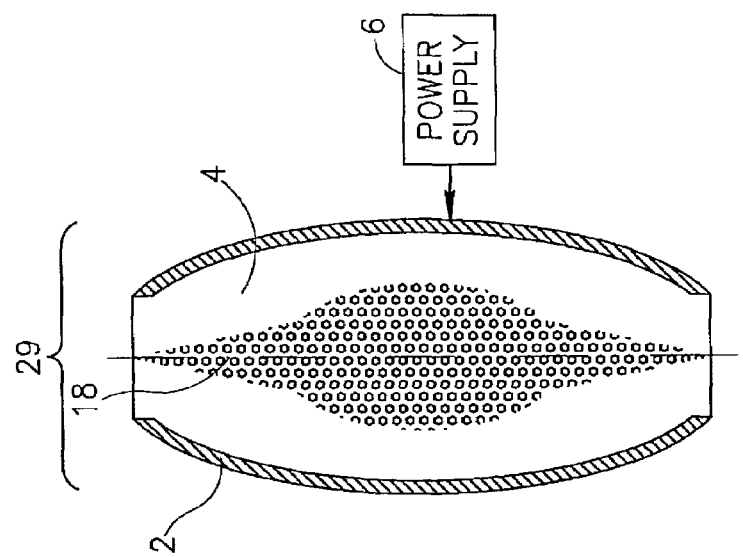
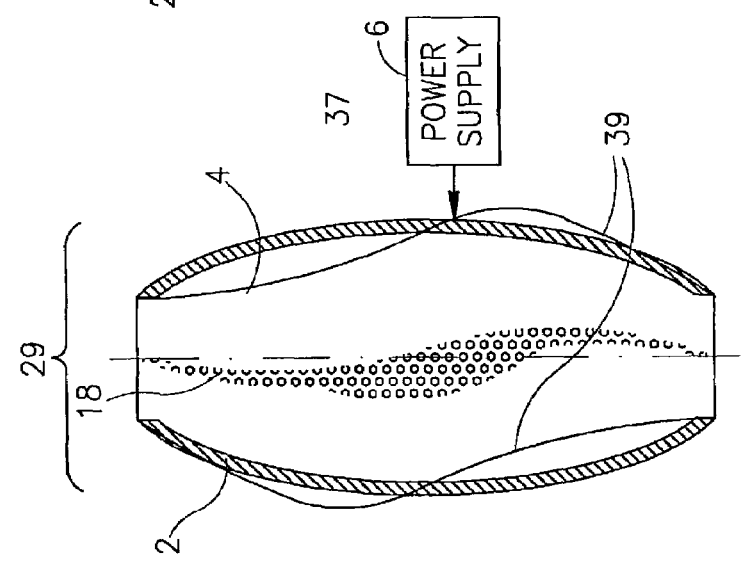
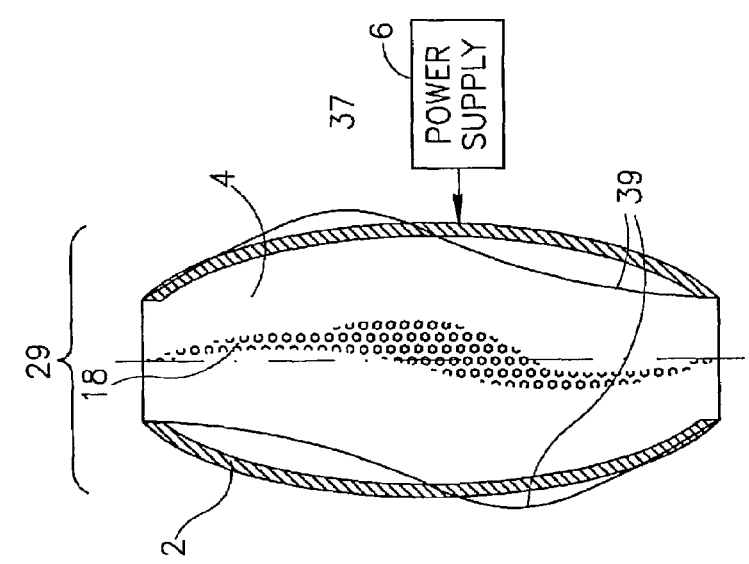

FIG.31

| NO. OF THE SAMPLE | M02524 | M02525 | M02526 | M02527 | M02528 | M02529 |
|---|---|---|---|---|---|---|
| SAMPLE DESCRIPTION | WATER NO. 1 | WATER NO. 2 | WATER NO. 3 | WATER NO. 4 | WATER NO. 5 | WATER NO. 6 |
| ANALYSIS PER | | | | | | |
| TOTAL COUNT CFU/1ml | $9.8 \times 10^4$ | $1.3 \times 10^3$ | $8.7 \times 10^4$ | $7.0 \times 10^4$ | $5.1 \times 10^4$ | <100 |

FIG.32

| LAB NO. | SAMPLE | BACTERIA COUNT CFU/1ml | MOLD COUNT CFU/1ml |
|---|---|---|---|
| 2717 | TREATMENT NO. 1 | $8.6 \times 10^3$ | <10 |
| 2718 | TREATMENT NO. 2 | $4.1 \times 10^6$ | <10 |
| 2719 | TREATMENT NO. 3 | $1.2 \times 10^7$ | <10 |
| 2720 | TREATMENT NO. 4 | $1.2 \times 10^8$ | $3 \times 10^4$ |
| 2721 | TREATMENT NO. 5 | <10 | <10 |
| 2722 | CONTROL NO. 6 | $4 \times 10^8$ | $4.2 \times 10^5$ |

APPARATUS FOR STERILIZING A LIQUID WITH FOCUSED ACOUSTIC STANDING WAVES

PRIOR APPLICATION DATA

The present application claims priority from provisional application Ser. No. 60/324,281, filed on Sep. 25, 2001.

FIELD OF THE INVENTION

The present invention relates to methods and apparatuses for sterilization of liquid, and more particularly, to such a method and apparatus that utilizes hydrodynamic focused and scanning cavitation.

BACKGROUND OF THE INVENTION

Various methods have been employed for sterilization and purification of liquid. For example, UV radiation, disinfection by biocides and pasteurization have been used for water sterilization. Ultraviolet (UV) treatment has been used to disinfect clear water as described in U.S. Pat. Nos. 3,634,025; 3,700,406; 3,837,800; 3,889,123; 3,894,236; 4,471,225 and 4,602,162. Each of these U.S patents describes a method for sterilization of water-based fluids. The principal idea behind these techniques is typically that UV radiation penetrates the clear liquid to kill offending microorganisms. UV has been also used in combination with magnetic treatment (e.g. U.S. Pat. No. 5,997,812) by passing the fluid through a magnetic field followed by exposure of the fluid to a disinfecting amount of ultraviolet radiation. The conventional technology of UV treatment is limited because systems made of quartz have a tendency to foul easily and maintenance costs are high.

Another approach to disinfect water is by adding appreciable levels of various biocide fluids to kill and inhibit the growth of microorganisms (e.g. U.S. Pat. No. 3,230,137). However, people exposed to biocides may experience allergic reactions or other problems. In short, although bacterial counts can be reduced over the short term, biocides are often more problematic than the microorganisms themselves.

Another method for the disinfection of fluids is pasteurization. In this process, fluids are heated to a pasteurizing temperature for a required period of time and subsequently cooled to an operating temperature. This process is energy intensive and the costs resulting from the heating and cooling steps are high.

Various other methods for sterilization such as sterilization by ozone or $H_2O_2$ exist, however, these are either expensive, hazardous or not sufficiently effective.

SUMMARY OF THE INVENTION

Embodiments of the present invention provide apparatus and methods for liquid sterilization based on focused acoustic vibration waves created in the liquid.

Embodiments of the invention relate to an apparatus and system for sterilization of liquid including at least one container suitable for containing a liquid and including an ultrasonic vibratable element.

According to further embodiments of the present invention the system may further include a power supply system operatively connected to the vibratable element. The power supply system may be adapted to supply electric waves having a preselected frequency or frequency range to the vibratable element.

According to some embodiments of the present invention the ultrasonic vibratable element may include a piezoceramic material. The piezoceramic material may be at least partially coated with a substantially conductive material. The conductive material may be operatively connected to the power supply system.

According to some embodiments of the present invention, the electric waves produced by the power supply system may have a frequency that substantially matches the resonance frequency of a system formed by the liquid, the cavity within which the liquid resides and the ultrasonic vibratable element. The electric wave may cause the ultrasonic vibratable element to oscillate. The oscillation of the vibratable element may be dependent upon the frequency or the frequency range of the electric waves, which may either be continuous or of a pulsing nature. In one embodiment, the electric waves may have a frequency that substantially matches the resonance frequency of the system comprising the liquid, the cavity and the piezoceramic material that may be included in the ultrasonic vibratable element.

According to some embodiments of the present invention the focused and scanning ultrasonic vibratable element may be adapted to cause liquid to vibrate at a preselected frequency or frequency range.

According to further embodiments the focused and scanning vibratable element may include a piezoceramic ring at least partially coated on the outer surface with a conducting material, and having various shapes, for example, cylindrical, convex, concave or tapered.

Some embodiments of the present invention also relate to a method for sterilization of liquid, the method including placing liquid in a container including at least one ultrasonic vibratable element, applying to the vibratable element electric waves at the frequency resonance of the vibratable element and of the liquid and producing acoustic vibration waves in the liquid.

BRIEF DESCRIPTION OF THE DRAWINGS

The present invention will be understood and appreciated more fully from the following detailed description taken in conjunction with the appended drawings in which:

FIGS. 16A-16C are schematic illustrations of produced cavitation patterns in a convex piezoceramic ring when applying the second mode wave pattern of longitudinal vibrations according to an embodiment of the present invention;

FIGS. 31-32 are microbiological examination reports; and

Figure 1A:
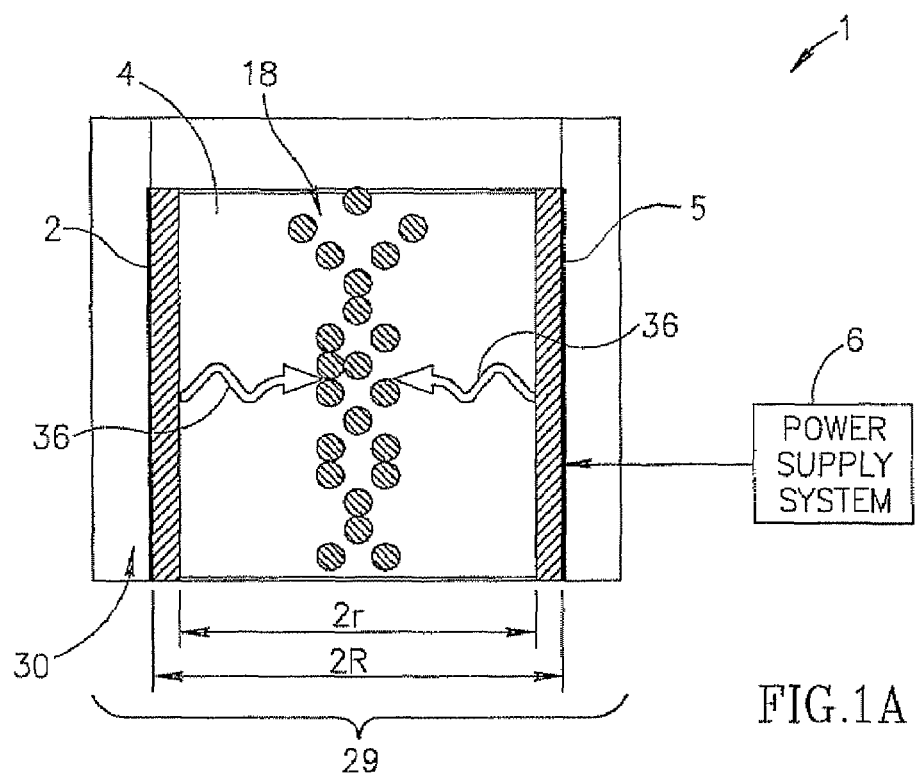
FIGS. 1A-1E are schematic illustrations of embodiments of a sterilization system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well known features may be omitted or simplified in order not to obscure the invention.

Embodiments of the invention are directed towards methods and apparatuses for liquid sterilization. Embodiments of the invention provide methods and systems for the sterilization of non-flowing and flowing liquid.

Embodiments of the present invention may be directed towards an ultrasonic vibratable element. Such a vibratable element may include a piezoceramic material. The piezoceramic material may be selected from a group of piezoceramic materials including, but not limited to PZT-4, PZT-8, APC840, APC841, APC850, APC855, APC880 and APC856. However it should be noted that the vibratable element of embodiments of the present invention is not limited to include a piezoceramic material and other suitable material may also be used.

Figure 1B:
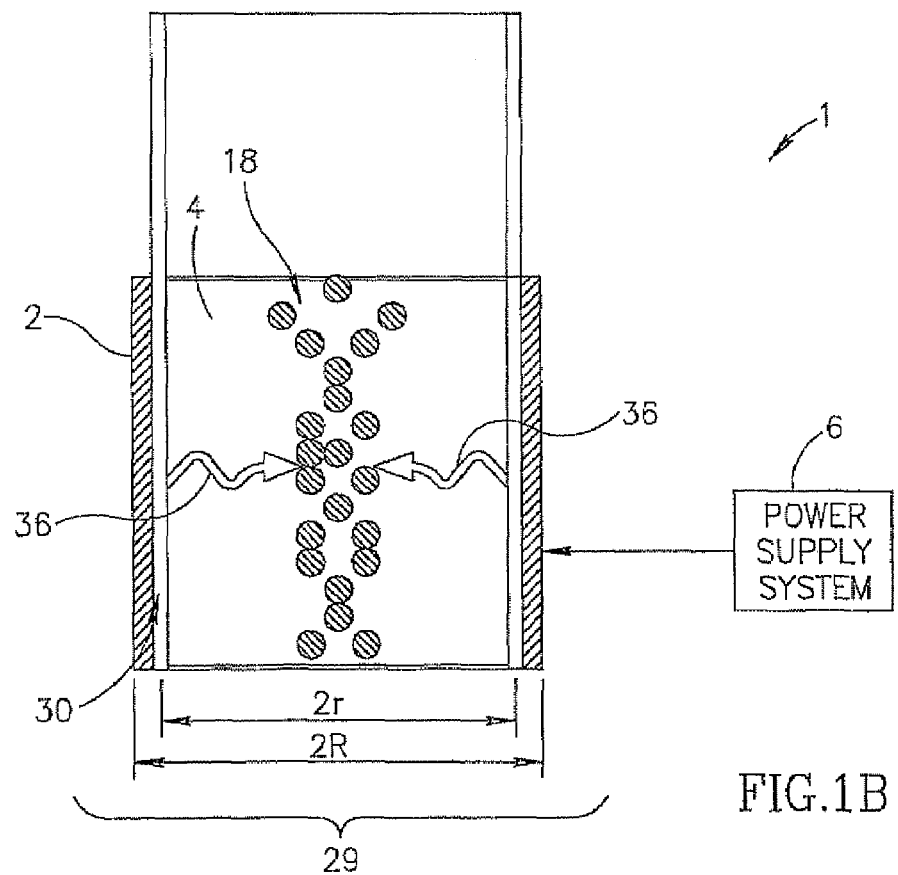

Reference is now made to FIGS. 1A and 1B, which illustrate a longitudinal cross section of one embodiment of a sterilization system 1. In the embodiment shown, sterilization system 1 may include a power supply system 6, for thickness mode vibration, and a container 29. The container 29 may be adapted to contain liquid 4, for example water, milk, juice, and any other thin or viscous liquid which may be consumed. The container 29 may include an ultrasonic vibratable element 2. The vibratable element 2 may include a piezoceramic material, such as PZT-4 or PZT-8 (Morgan Matroc Inc. Bedford Ohio) or any other piezoceramic material for example APC840, APC841, APC850, APC855, APC880 and APC856 (American Piezoceramic Inc.) and others.

FIGS. 1A and 1B present an embodiment of the invention for the sterilization of flowing liquid. The container 29 may be, for example, a tube 30 having a ring of piezoceramic material 2 but may have other shapes as required. Container 29 is typically made of rubber, plastic, silicone or metal but may be made of any other suitable material. The ultrasonic vibratable element 2 may be coated with a conducting material 5. The conducting material 5 may be selected from a group of conducting materials including, but not limited to, silver, gold, nickel, conducting rubber or any other compatible conducting material.

Figure 1C:
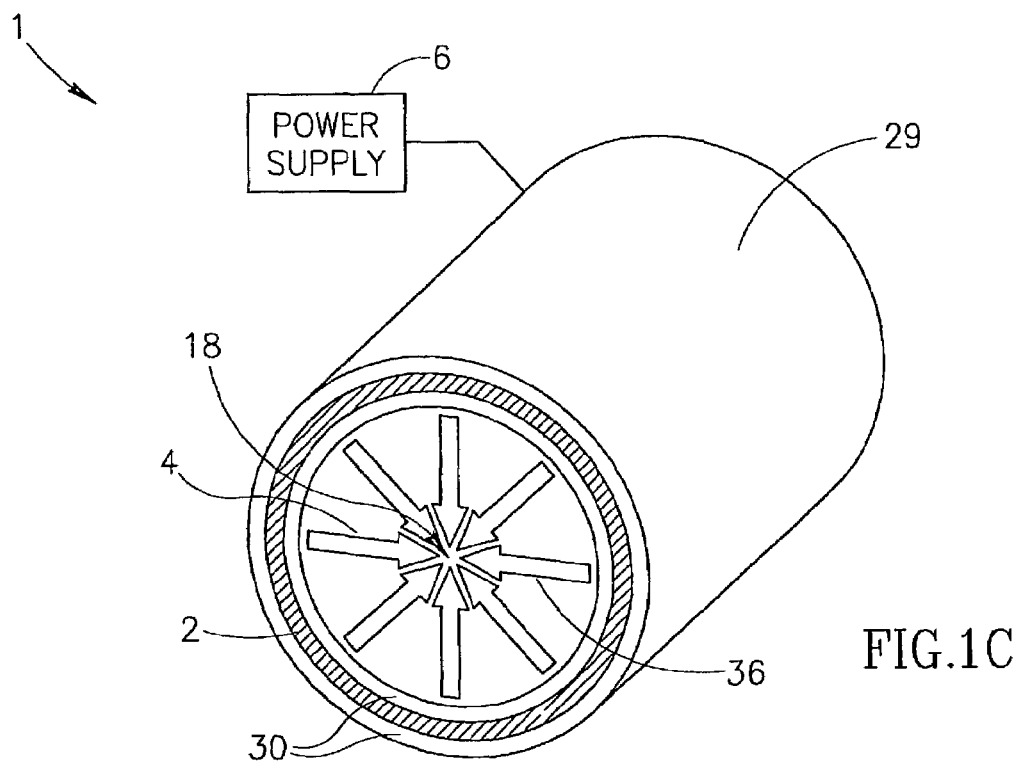

The vibratable element 2 may be attached to the inner portion of tube 30 as in FIG. 1A or to the outer portion of tube 30 as in FIG. 1B or it may be fitted between an inner tube and an outer tube substantially surrounding the inner tube, as illustrated in three dimensions in FIG. 1C. The minimal thickness of the vibratable element 2, illustrated by R-r, may be in the order of 0.05 mm to 0.1 mm and the maximal thickness may be in the order of 20-50 mm. The inner radius of the vibratable element 2 (r) may be in the order of 1-100 mm. The length of the vibratable element may be in the order of 1-1000 mm. Other dimensions may be applied.

Figure 1D:
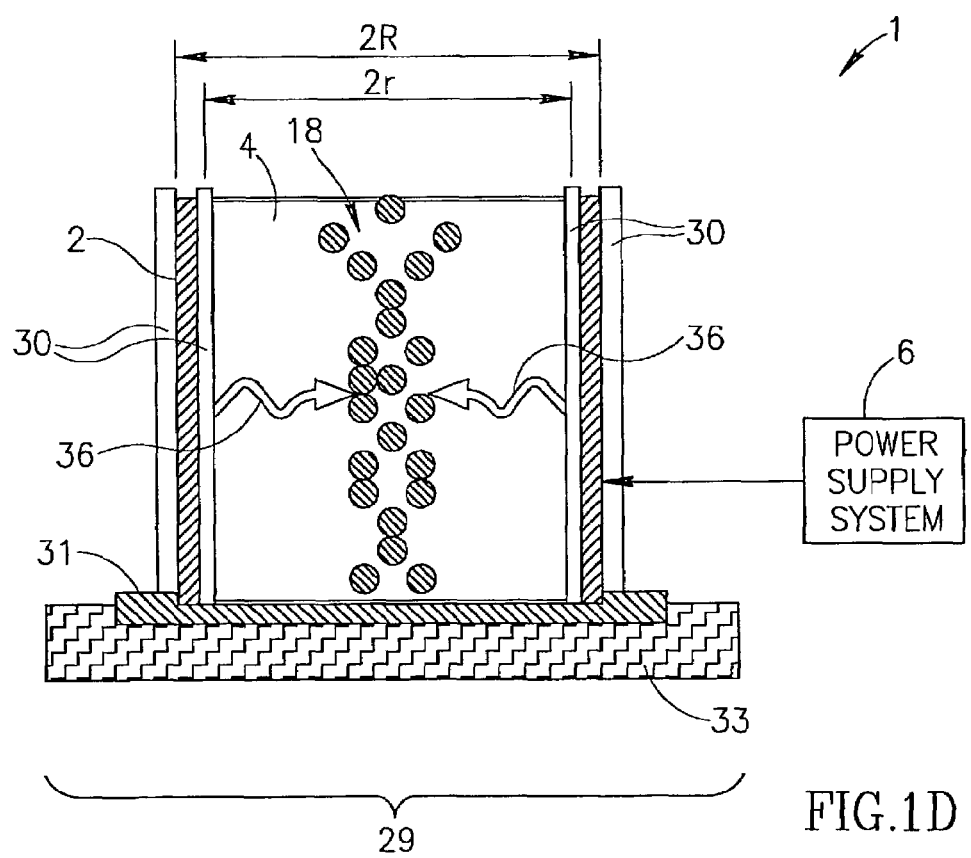
Figure 1E:
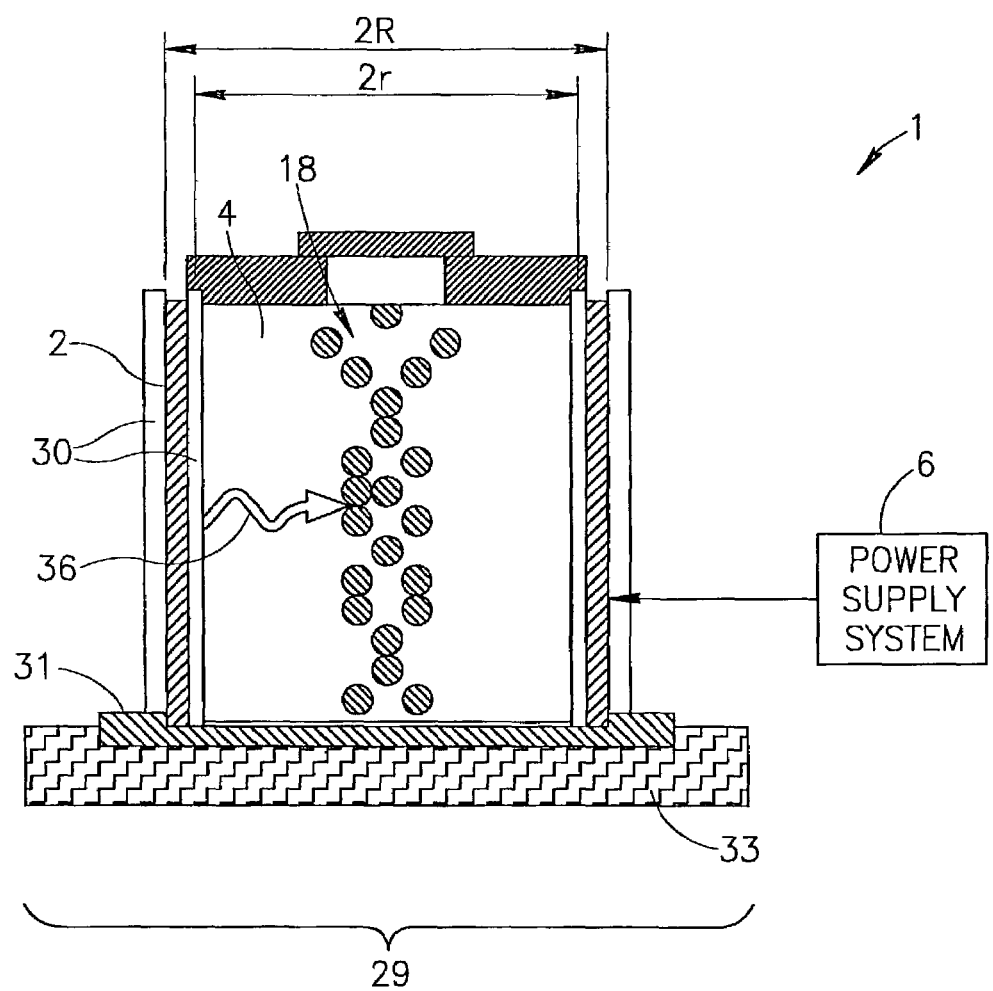

FIGS. 1D and 1E present another embodiment of the invention for the sterilization of non-flowing liquid. Container 29 may be a vessel 31, which may be a cylindrical tube closed at least at one end to contain a substantially non-flowing body of liquid. Vessel 31 may include a vibratable element 2. The vibratable element 2 may be attached, for example, to the outer or inner portion of the cylindrical section of vessel 31 or between an inner tube and an outer tube substantially surrounding the inner tube, as present in FIGS. 1D and 1E. Vessel 31 may be made of rubber, plastic, silicone, metal, glass, etc. Alternatively, vessel 31 may be made of any other suitable material, for example piezoceramic material. The Vessel 31 may be open or closed at least at one side as illustrated in FIGS. 1D and 1E. Vessel 31 may further include an outer layer 33. The outer layer 33 may include an adsorbing material 33 such as rubber, silicone, polymer or metal or any other suitable absorbing material. The absorbing material 33 may be adapted to absorb the acoustic vibrations, such that the overall system remains stable.

Power supply system 6 may be adapted to supply electric input to the vibratable element 2. The frequency of the electric input may be selectively controlled.

Electric input from the power supply 6 may be delivered to the conductive material of the vibratable element 2, which may then cause substantially ultrasound waves in the vibratable element 2. For example, the electric input delivered to the vibratable element 2 may cause thickness waves, longitudinal waves, waves that cause torsion in vibratable element 2 or any other acoustic waves.

In one embodiment of the invention the sterilization may be achieved by supplying electric waves from the power supply system 6 to the vibratable element 2 in a direction that is substantially through the thickness of vibratable element 2. In this embodiment the selected frequency or frequency range of the electric waves supplied to the vibratable element 2 by the power supply system 6 may be in the MHz range. The selected frequency may be dependent upon various system 1 parameters, including, but not limited to the thickness of the vibratable element (e.g. the ceramic thickness of the piezoceramic material). For example, the frequency applied to a piezoceramic ring 2 with a thickness of 0.05 mm may be approximately 20 MHz and the frequency applied to a piezoceramic ring 2 with a thickness of 50 mm may be approximately 0.1 MHz. Other frequencies and thicknesses may be selected.

In one embodiment of the invention the sterilization may be achieved by applying a combination of two or more frequencies or frequency patterns of electric waves. For example, electric waves having a frequency in the KHz range may be supplied in the longitudinal direction, i.e., parallel to the length of the vibratable element 2. Electric waves having a frequency typically in the MHz range may be supplied trough the thickness of the vibratable element 2 as was described above for the thickness sterilization system. The frequency of the KHz electric waves may depend upon the thickness and length of the piezoceramic ring, and is typically between 20-500 KHz. Other frequencies and thicknesses may be selected.

In one embodiment of the invention the sterilization may be achieved by applying a combination of three or more frequencies of frequency patterns of electric waves. The first two wave patterns may be supplied in the substantially longitudinal sterilization system, described above, e.g. the thickness waves and the longitude waves. The third wave pattern may be in the KHz range, typically between 15 to 300 KHz and may applied substantially through the thickness of the vibratable element 2 in addition to the two wave patterns supplied to the longitudinal sterilization system.

In response to the electric input generated by power supply system 6, the vibratable element 2 may oscillate, and may focus the center of the vibrating elements ultrasonic waves as depicted by arrow 36. For example, in response to the electric input the piezoceramic material that may be included in the vibratable element 2 may ultrasonically vibrate. These focused ultrasonic waves may initiate pressures in excess of several atmospheres, or bars, within the liquid, which pressures may cause the sterilization of the liquid 4. Without limiting the invention in any way, the sterilization of the liquid may be explained by the following: the progression of the ultrasound waves may create negative pressure in the liquid. The negative pressure may cause cavitation bubbles 18 (FIGS. 1A-1E) in the liquid to form. The cavitation bubbles 18 may expand to an unstable size, and may eventually collapse. The collapse of the cavitation bubbles may generate relatively high pressure and temperature in the liquid that may lead to the breakage of microorganisms, and thus may lead to the sterilization of the liquid. Furthermore, pressure within the liquid caused by resonance of high frequency ultrasonic vibrations may also contribute the destruction of micro-organisms within the liquid.

Figure 2A:
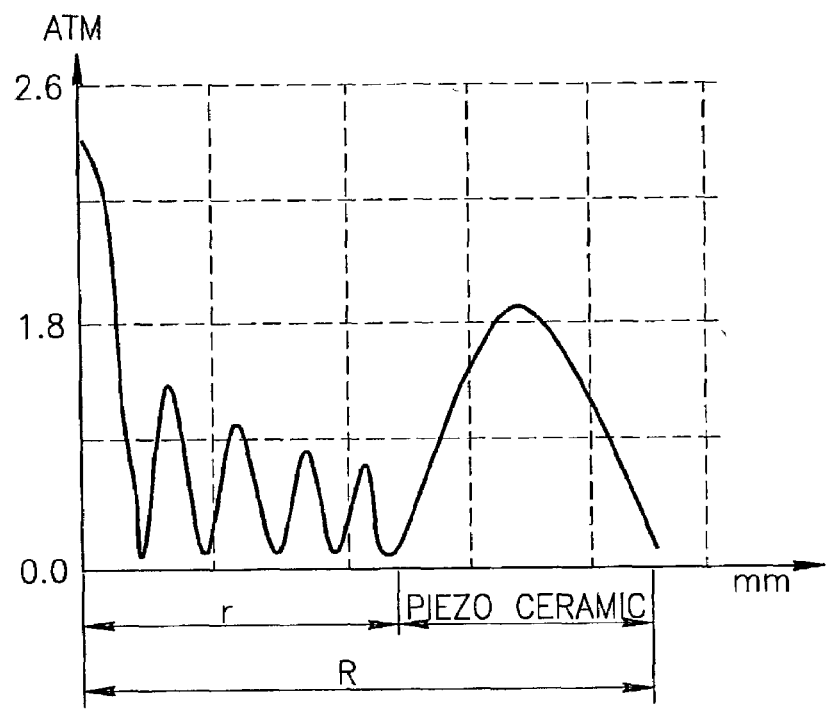
FIGS. 2A-2B are graphic illustrations of the pressure as a function of the distance from the cylinder axis for a ring of piezoceramic material according to an embodiment of the present invention.
Figure 2B:
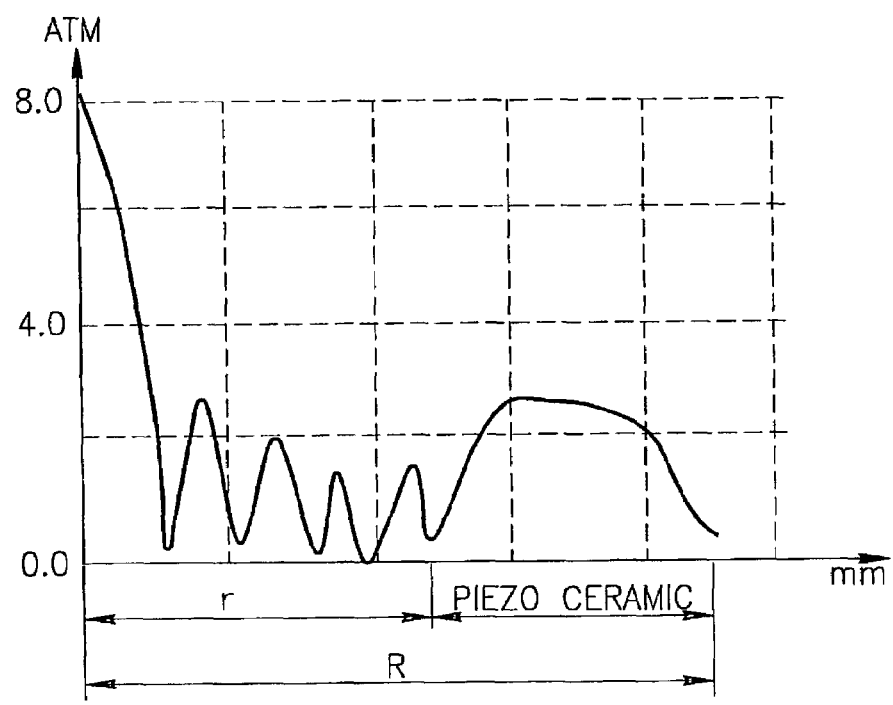

Reference is now made to FIGS. 2A and 2B, which are graphic illustrations of the pressure as a function of the distance from the cylinder axis of a ring of piezoceramic material, according to an embodiment of the present invention. The pressure data was measured for a system including a cylindrical container 29, having an inner piezoceramic ring 2 with an outer radius of r=20 mm, and which contains water, as described in FIGS. 1A through 1E. This pressure may develop due to vibration waves as depicted by arrow 36 that may be generated by piezoceramic ring 2 as illustrated in FIG. 1.

In FIG. 2A, electric waves having a frequency of 1.25 MHz and a potential of 1 Volt, which may be the-resonance frequency of a piezoceramic material, may be supplied to the vibratable element 2. Other frequencies may be used as appropriate. The electric waves supplied in this frequency may generate a pressure of approximately 2 atmospheres in the piezoceramic material (R-r in the graph) and the piezoceramic material may oscillate. The oscillation may cause vibrational waves, as depicted by arrow 36 in FIG. 1, in the liquid, causing a pressure of approximately 2.5 atmospheres in the water at the middle axis (R=O) of container 29.

In FIG. 2B, the frequency of the electric waves may be 1 MHz, at a potential of 1 Volt, which may frequency may be the system's resonant frequency. The system frequency resonance is the frequency at which a resonance may be achieved for the piezoceramic material and the water for specific physical conditions of the system. As a result of the supplied system resonance frequency a pressure of above 8 atmospheres may develop in the water at the middle axis (R=O) of container 29.

By matching the supplied frequency to the system resonance frequency the pressure developed in the water at the middle of the container may considerably higher than when the frequency matches the piezoceramic material resonance alone. Thus, the highest efficiency of sterilization may be achieved when the electric input is compatible to the system frequency resonance.

Figure 3A:
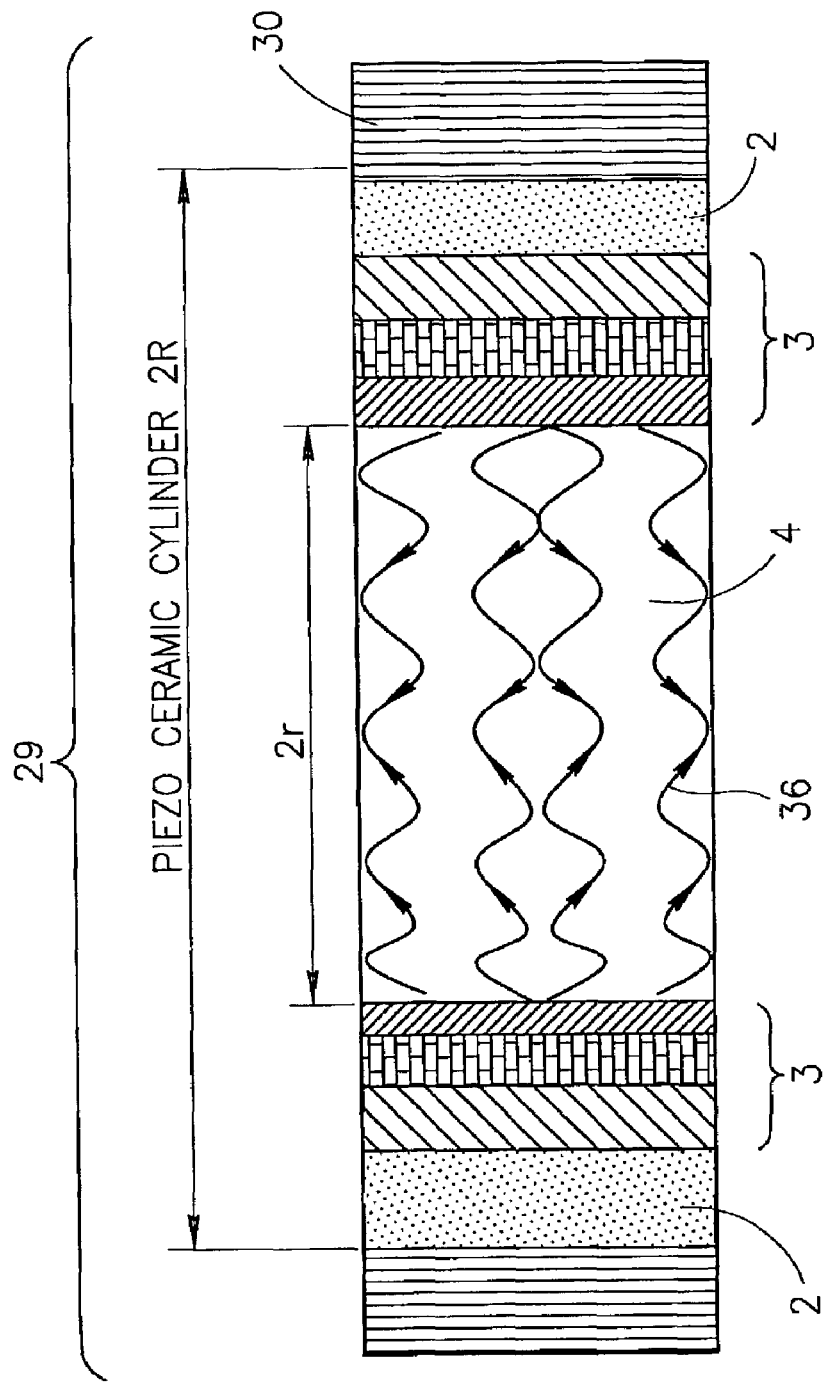
FIGS. 3A-3B are schematic and graphic illustrations of a piezoceramic ring including a matching layer according to an embodiment of the present invention.
Figure 3B:
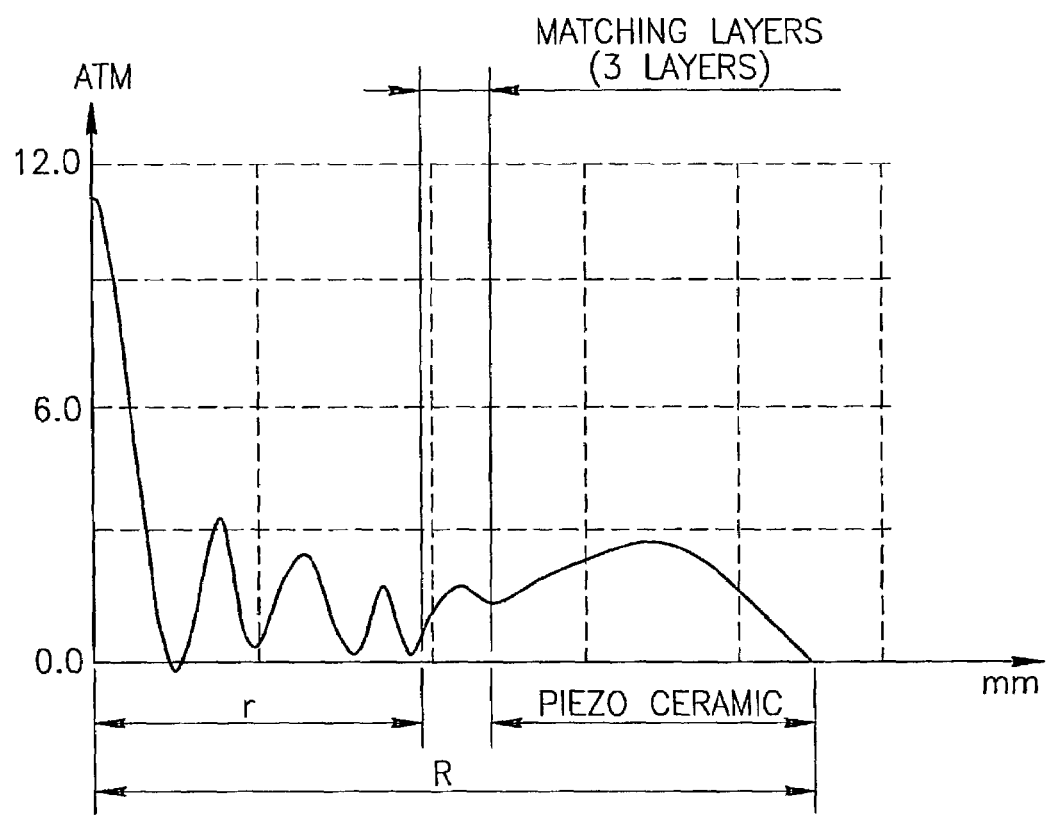

Reference is now made to FIGS. 3A-3B which are schematic and graphic illustrations of a vibratable element including a matching layer according to an embodiment of the present invention.

FIG. 3A is a longitude cross section of a part of container 29. Container 29, which contains liquid 4, comprises a vibratable element 2, with additional inner layers of matching material 3 and an outer tube 30. The matching material may be silicone, but can be any other compatible material. The matching material may be constructed as one or more layers, as illustrated in FIG. 3A, on the inner side of the vibratable element 2. Each layer of matching material may have a different thickness or may be made of a different kind of material or materials. The matching layer may also be an inner tube. The thickness of the matching layer may depend on the thickness of the vibratable element 2, on the thickness of the piezoceramic material included therein, and/or on the applied frequency. According to some embodiments the thickness of the matching layer is typically between 0.1 to 100 times the thickness of the vibratable element 2. According to further embodiments of the present invention the thickness of the matching layer is typically between 0.1 to 100 times the thicknesses of the ceramic layer. FIG. 3B is a graphical illustration of the pressure in atmospheres, generated within a container 29 with a radius of R=20 mm, having a vibratable element 2 and a layer of matching material 3 and which contains water, as described in FIG. 3A. This pressure may be developed due to vibration waves as depicted by arrow 36 in FIG. 3A progressing through the thickness of piezoceramic ring, and through the water.

The layer of matching material 3 may be adapted to gradually reduce the velocity of the vibrational waves between the velocity of the wave in the piezoceramic material (which may be approximately 3500-4500 m/sec but may be any other frequency) and the velocity of the wave in the liquid (which is for water 1560 m/sec), thus potentially minimizing the loss of energy due to drastic velocity changes.

By adding a layer of matching material between the piezoceramic ring and the water, and applying a signal of 1.1 MHz at a potential of 1 Volt, a pressure of approximately 12 atmospheres may be developed in the middle portion of the container. This pressure may be considerably higher than the pressure of 2.5 atmospheres developed when using a ring of piezoceramic material alone as illustrated in FIG. 2A.

Figure 4:
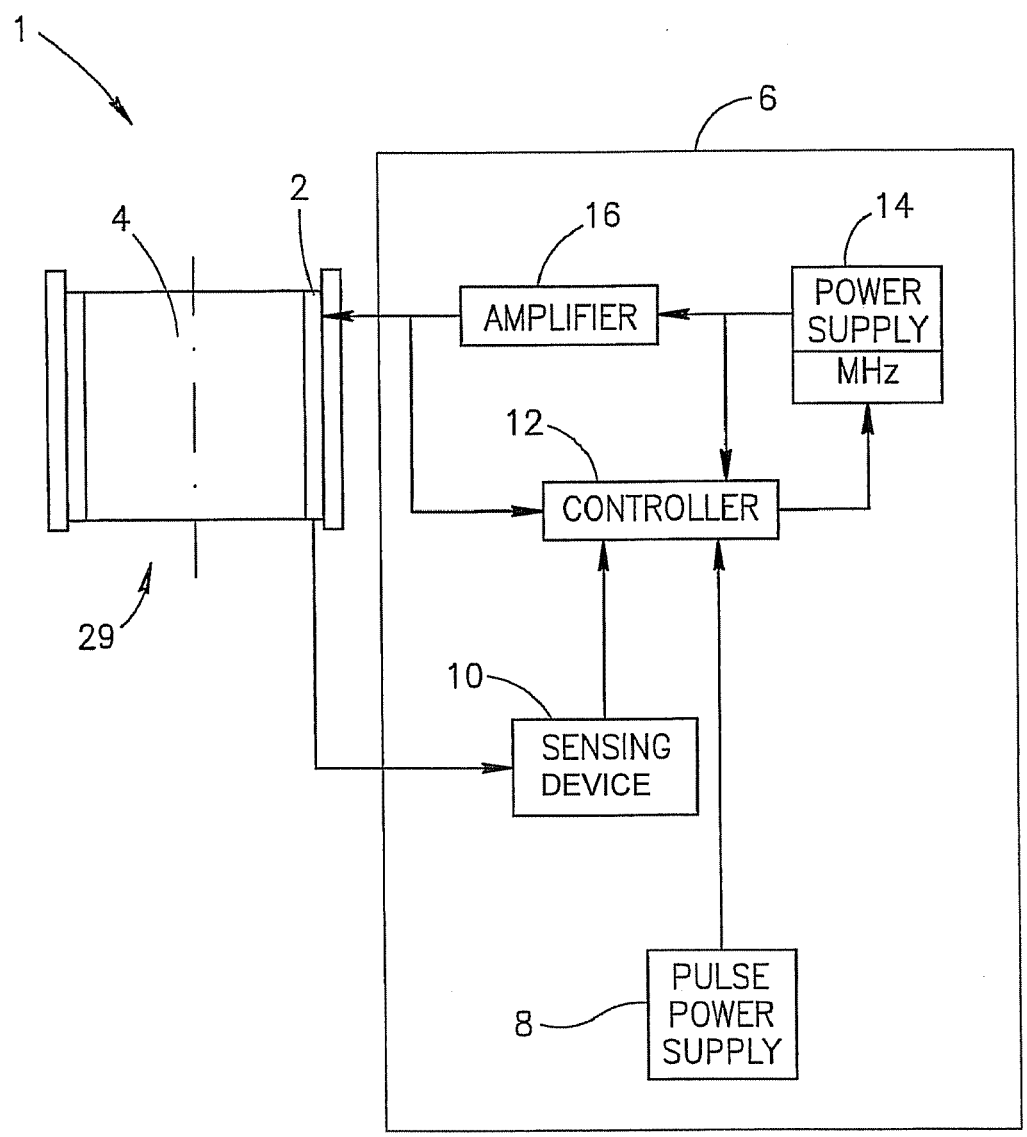
FIG. 4 is a schematic illustration including a block diagram illustration of a sterilization system according to one embodiment of the present invention wherein thickness mode vibrations are applied.

Reference is now made to FIG. 4, which is a schematic illustration including a block diagram illustration of a sterilization system according to one embodiment of the present invention wherein thickness mode vibrations are applied. Sterilization system 1 may include a container 29 with liquid 4 therein. Container 29 surrounds a vibratable element 2 including a piezoceramic material that is coated on the outer side, by a conducting material. The conducting material may be operatively connected to a power supply system 6.

Power supply system 6 may include the following: a pulse power supply 8, a MHz power supply 14, an amplifier 16, a controller 12, and a sensing device 10. Pulse power supply 8 may be adapted to provide electric waves to the piezoceramic vibratable element 2, possibly after amplification by amplifier 16. Sensing device 10 may be adapted to sense various system parameters, for example the sensing device 10 may be adapted to sense the resulting oscillation frequencies in the liquid. Controller 12 may be configured to receive input from sensing device 10 (e.g. oscillation frequencies in the liquid) and may issue control signal to the power supply 14 to supply electric waves having a desired frequency for obtaining frequency resonance in the vibratable element 2 and the liquid 4, thus possibly achieving high pressure in liquid 4 at the middle axis of container 29. The power supply system 6 may or may not supply a signal at a resonance frequency of the vibratable element 2 and the liquid 4. In alternate embodiments the sensing device 10 need not be used or may be omitted altogether.

Figure 5A:
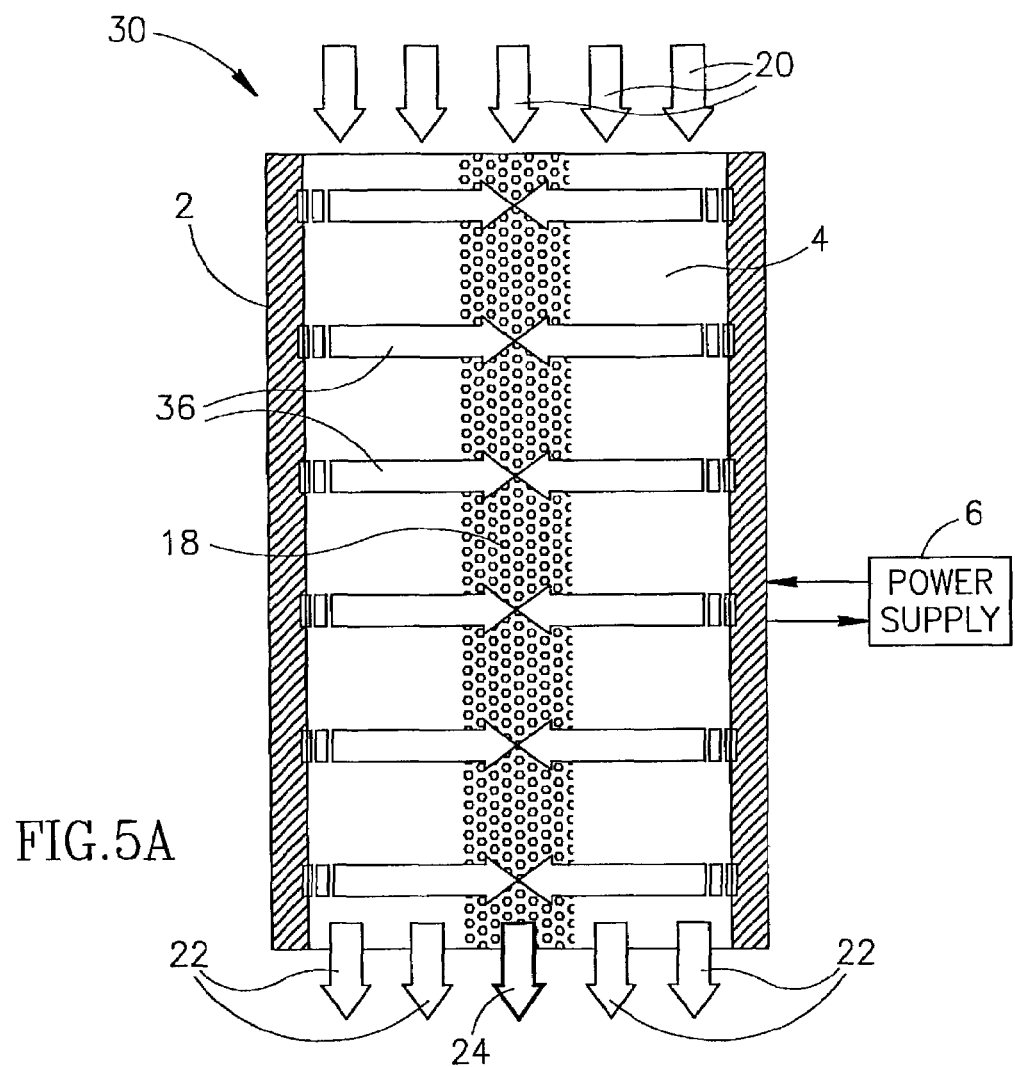
FIGS. 5A-5B are schematic illustrations of a produced focused cavitation pattern in a cylindrical piezoceramic ring according to an embodiment of the present invention.
Figure 5B:
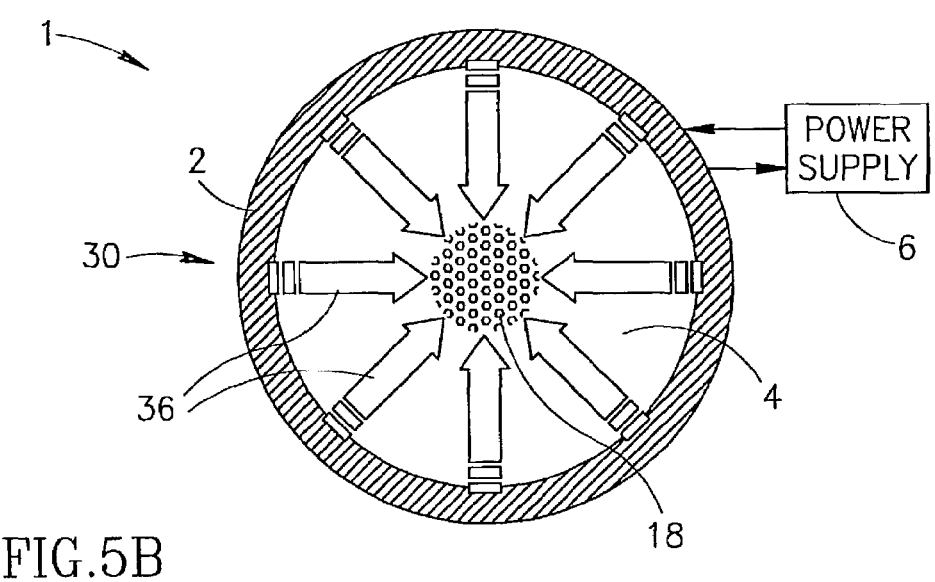

Reference is now made to FIGS. 5A and 5B, which are schematic illustrations of a produced cavitation pattern in a cylindrical piezoceramic ring according to an embodiment of the present invention. Cavitation pattern 18 produced for a cylindrical piezoceramic ring 2 used in the sterilization system described in FIG. 4. Other embodiments are possible as well, as will be described in greater detail hereinbelow.

FIG. 5A illustrates a longitudinal cross-section of tube 30, with liquid entering through the upper portion of the tube as depicted by arrow 20, and flowing through the tube 30. The power supply system 6 may be adapted to supply electric waves to a cylindrical piezoelectric ring 2 of tube 30. The supplied electric waves may cause vibrational oscillations as depicted by arrows 36, progressing from the piezoceramic ring 2 through the liquid 4. When a cylindrical shaped piezoceramic ring is used, the vibrations may be in the horizontal axis only. As a result of these vibrations, a high pressure area and cavitation bubbles 18, may be built up particularly, but not exclusively, in the middle region of tube 30. The high pressure and the cavitation may lead to the sterilization of the liquid 4 in the middle region of the tube 30. Thus, sterile liquid depicted by arrow 24, may exit the tube 30. Any liquid existing outside the cavitation and focus pressure region, as depicted by arrow 22, will not necessarily be sterilized. The size of the area of sterilized liquid 18 is dependent upon the voltage and frequency of the vibratable element 2.

FIG. 5B illustrates a horizontal cross section of the tube 30. The piezoceramic ring 2 may vibrate as a result of the electric waves supplied by the power supply system 6, and the vibrations depicted by arrows 36 may progress through the liquid 4 toward the middle section of the tube where high pressure and cavitation bubbles 18 may occur. In the case of a cylindrical piezoceramic ring, the horizontal cross section of the cavitation bubbles 18 may be a round circle in the center of tube 30 having a smaller diameter than the tube 30.

Figure 6A:
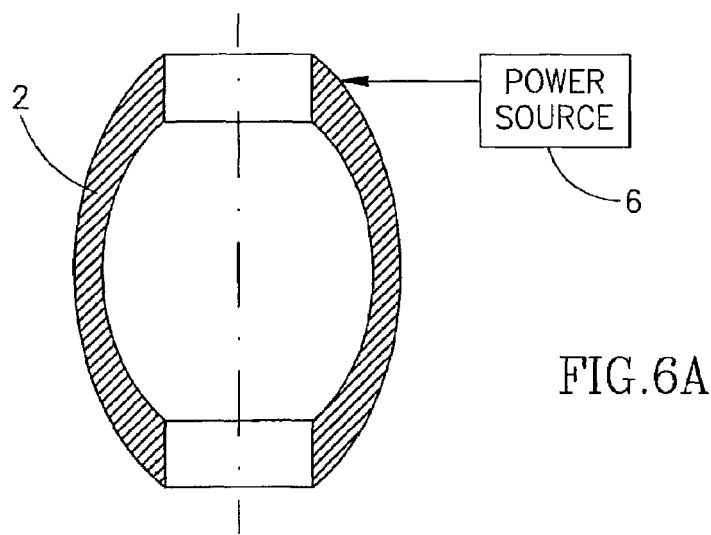
FIGS. 6A-6C are illustrations of various piezoceramic ring shapes according to some embodiments of the present invention
Figure 6B:
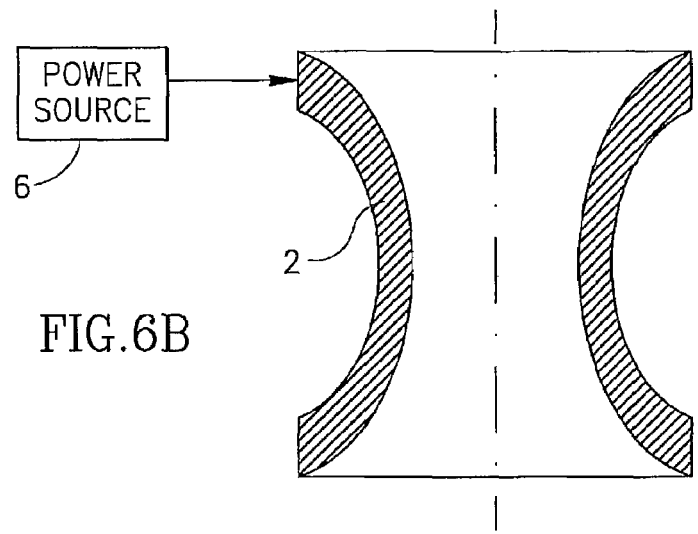
Figure 6C:
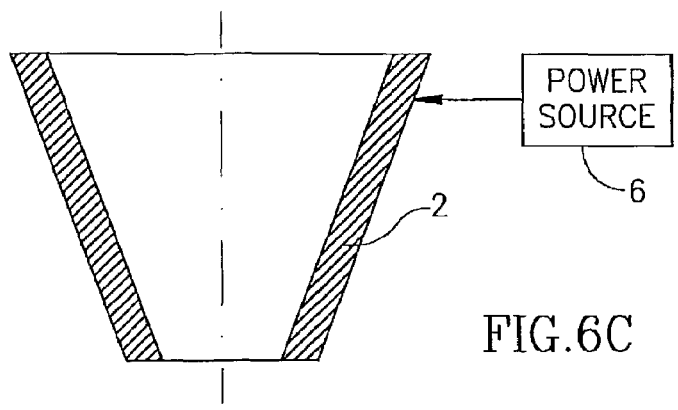

FIGS. 6A, 6B and 6C are illustrations of various piezoceramic ring shapes according some embodiments of the present invention. Container 29 or tube 30 and piezoceramic ring 2 may be further configured in any other suitable shape. With the various shapes different cavitation pattern achieved, as will be further discussed hereinbelow.

FIG. 6A is a longitudinal cross-section of a convex piezoceramic ring 2 according to some embodiments of the present invention, FIG. 6B is a longitudinal cross-section of a concave piezoceramic ring 2 according to some embodiments of the present invention, and FIG. 6C is a longitudinal cross-section of a tapered piezoceramic ring 2 according to some embodiments of the present invention. Each of these rings may be attached to an inner or outer portion of a container and may be connected to a power supply system 6.

Figure 7A:
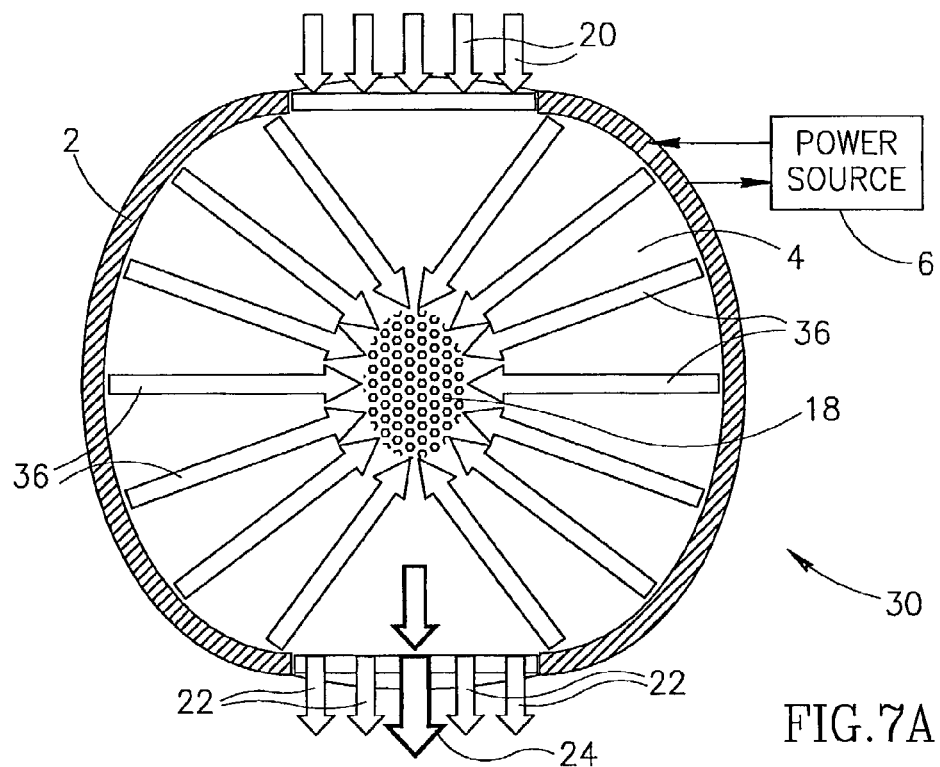
FIGS. 7A-7B are schematic illustrations of the produced focused cavitation pattern for a convex piezoceramic ring according to an embodiment of the present invention.
Figure 7B:
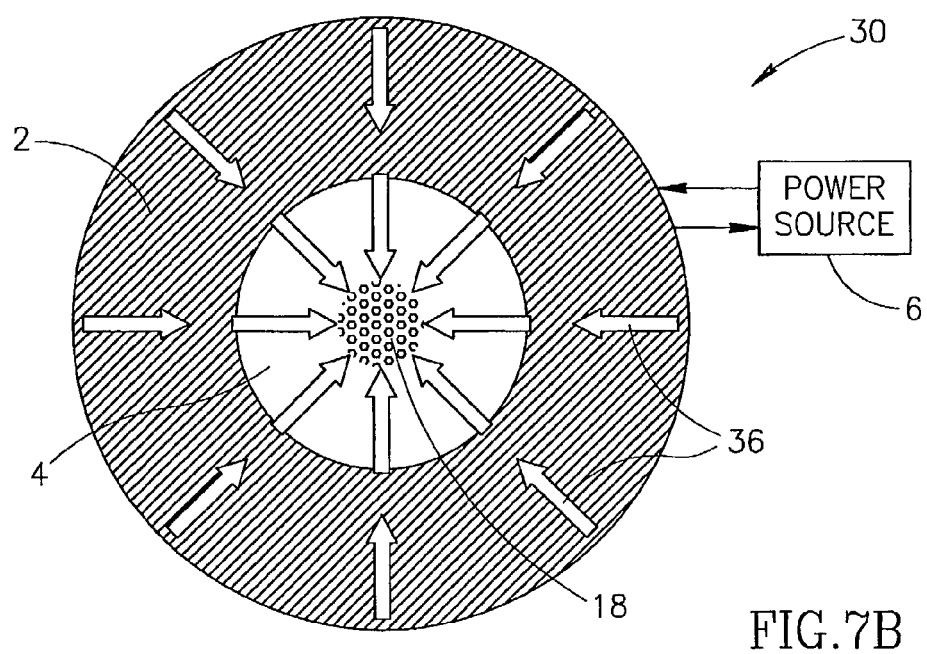

FIGS. 7A-7B are schematic illustrations of the produced cavitation pattern for a convex piezoceramic ring according to an embodiment of the present invention. According to the present embodiment, a convex piezoceramic ring 2 may be used in the thickness mode sterilization system described in FIG. 4. The longitudinal and horizontal cross sections of the convex piezoceramic ring are illustrated in FIGS. 7A and 7B.

Liquid may enter the upper portion of tube 30, as depicted by arrow 20, and may flow through it. The power supply system 6 may supply electric waves to the convex piezoceramic ring 2 in tube 30. The supplied electric waves may cause vibrational oscillations depicted by arrows 36, which may progress through the piezoceramic ring 2 and through the liquid 4. These vibrations may progress not only in the horizontal axis, as in the cylindrical piezoceramic ring, but also in other directions. As a result of these vibrations, an oval shaped high pressure area and cavitation bubbles 18 may be built up in the middle region of the tube. The high pressure and the cavitation may lead to the sterilization of the liquid in the oval region. Thus sterile liquid depicted by arrow 24 may exit the tube. The liquid 4 existing outside the cavitation region, as depicted by arrow 22, may not necessarily be sterile.

FIG. 7B illustrates a horizontal cross section of the convex piezoceramic ring. The convex piezoceramic ring 2 may vibrate as a result of the electric waves that may supplied by the power supply system 6, and the vibrations depicted by arrows 36 may progress through piezoceramic 2 and through liquid 4 toward the middle portion of the tube 30 where high pressure and cavitation bubbles 18 may occur. For the convex piezoceramic ring shape the horizontal cross section of the cavitation region may be a round circle in the center of the tube 30 having a smaller diameter than the tube.

Figure 8A:
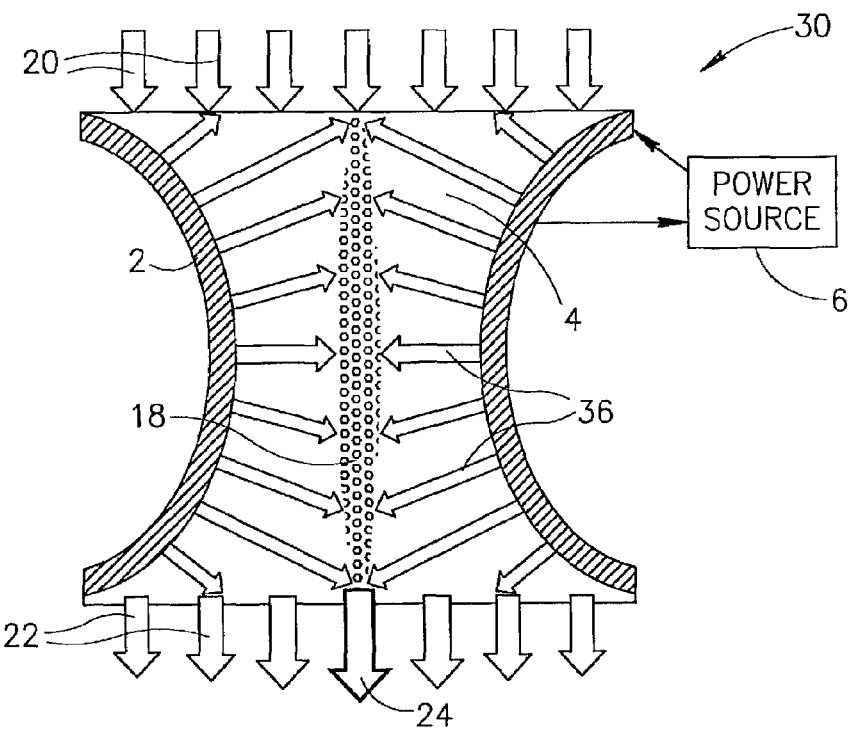
FIGS. 8A-8B are schematic illustrations of a produced focused cavitation pattern for a concave piezoceramic ring according to an embodiment of the present invention.
Figure 8B:
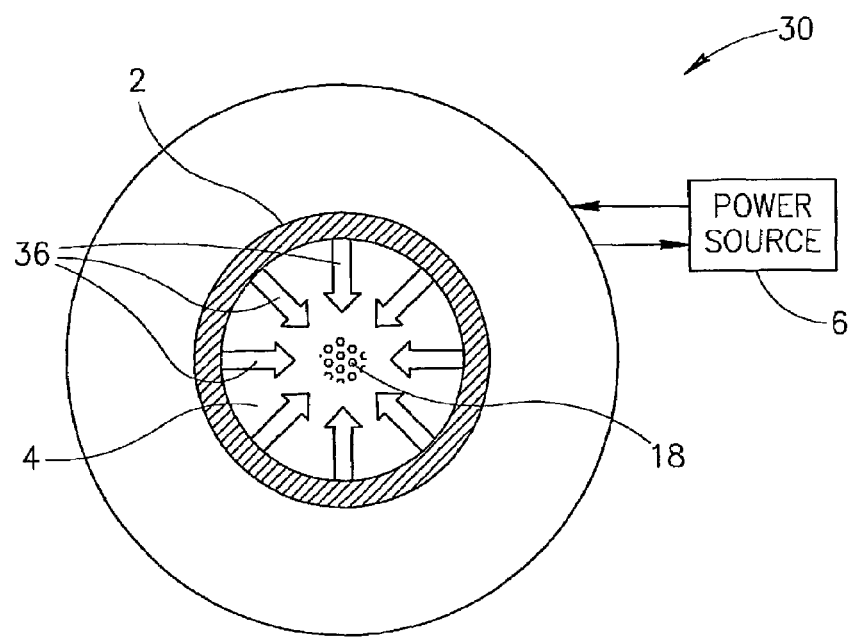

FIG. 8 illustrates a produced focus cavitation pattern according to another embodiment of the invention, wherein a concave piezoceramic ring 2 is used in the thickness mode sterilization system described in FIG. 4. The longitudinal and horizontal cross sections of the concave piezoceramic ring are illustrated in FIGS. 8A and 8B.

The system is similar to that described in FIGS. 7A and 7B. For the concave piezoceramic ring 2, the vibrations, depicted by arrow 36 may be in the horizontal axis as well as in other directions. The cavitation bubbles 18 may be obtained in a long narrow region at the middle portion of the tube 30. In the horizontal cross section of the concave piezoceramic ring 2 the cavitation bubbles 18 may be obtained in a small round circle in the middle portion of tube 30.

Figure 9A:
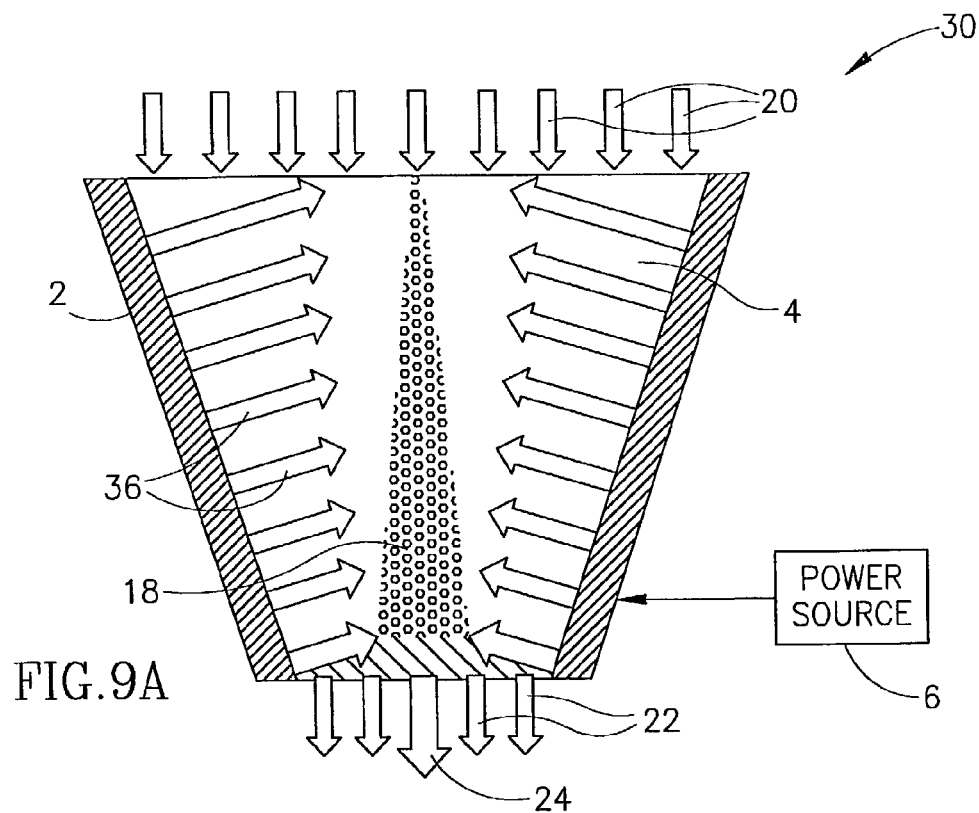
FIGS. 9A-9B are schematic illustrations of a produced focused cavitation pattern for a tapered piezoceramic ring according to an embodiment of the present invention.
Figure 9B:
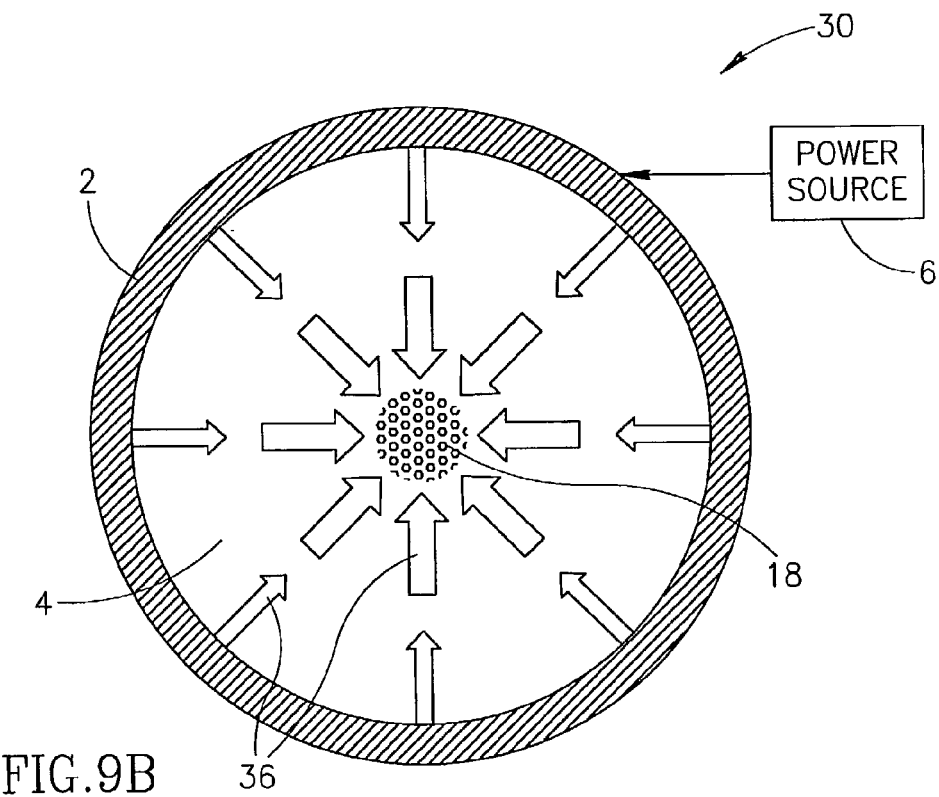

FIGS. 9A and 9B, illustrate the produced cavitation in a longitudinal and horizontal cross-section, according to another embodiment of the invention, wherein a tapered piezoceramic ring 2 is used in the thickness mode sterilization system described in FIG. 4.

The system is similar to that described in FIGS. 7A and 7B. For the tapered piezoceramic ring 2, the vibrations, depicted by arrow 36, may be in the horizontal axis as well as in other directions. The cavitation bubbles 18 may be obtained in a narrow conic region at the middle portion of the tube 30. In the horizontal cross section of the tapered piezoceramic ring 2 the cavitation bubbles 18 may be obtained in a small round circle in the middle portion of the tube.

Figure 10A:
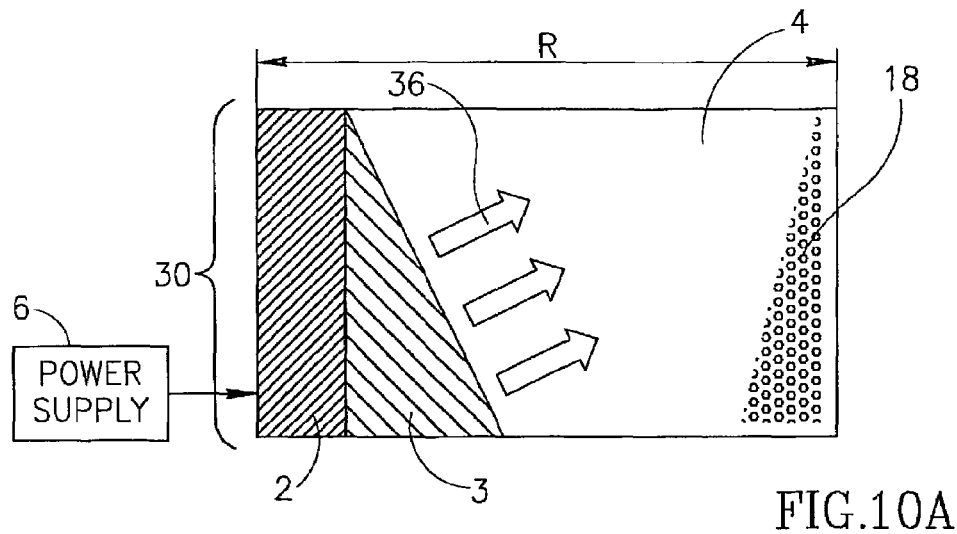
FIGS. 10A-10C are illustrations of various ring of matching layer shapes according to an embodiment of the present invention.
Figure 10B:
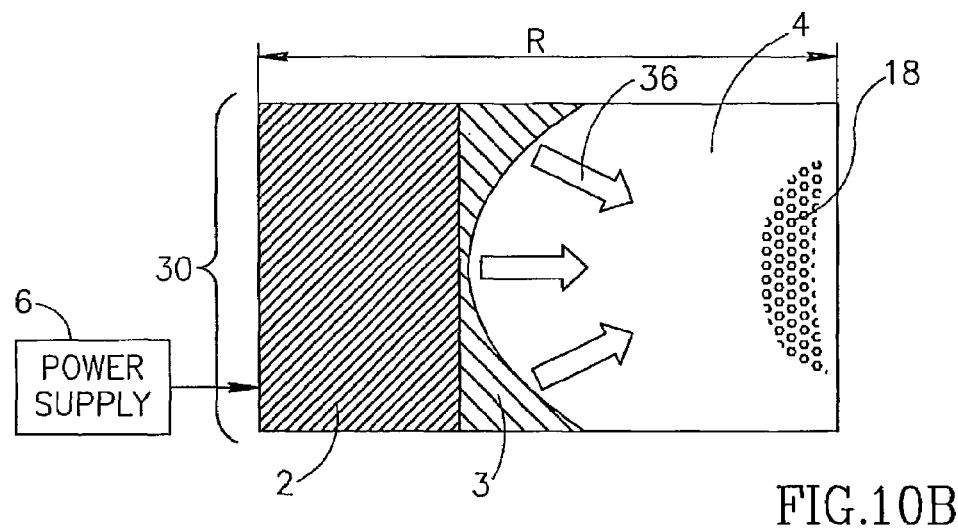
Figure 10C:
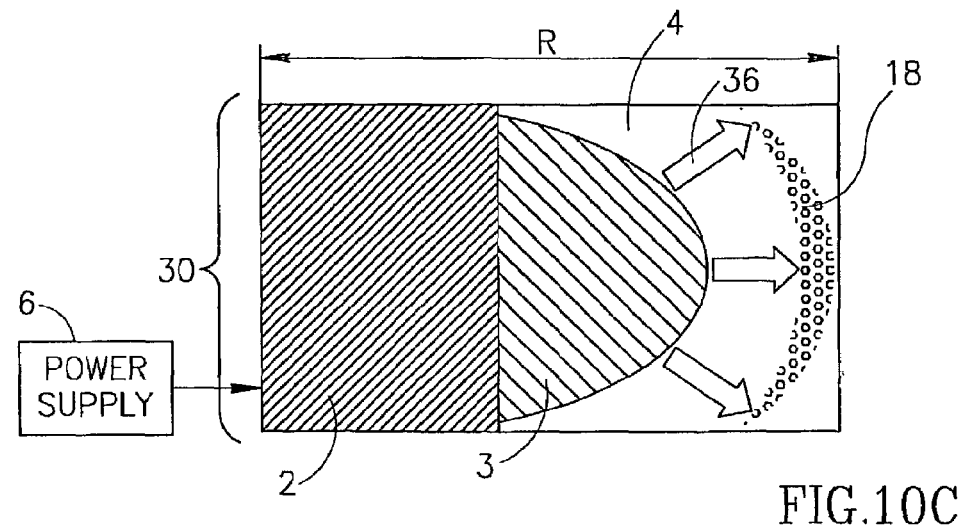

Reference is now made to FIGS. 10A-10C illustrating three further embodiments of the invention for various shapes of matching material layer. FIG. 10A illustrates tapered shape matching material layer, FIG. 10B illustrates concave shape matching material layer and FIG. 10C illustrates convex shape matching material layer. It will be appreciate that the layer of matching material 3 may be further configured in any other shape. FIGS. 10A-10C are a longitude cross section of half tube 30 (from R=O to R) having a cylindrical vibratable element including piezoceramic material 2, and including an inner layer of matching material 3. The vibratable element 2 may vibrate as a result of the electric waves supplied by the power supply system 6, and the vibrations, depicted by arrows 36, may progress through the liquid where high pressure and cavitation bubbles 18 may occur. Here the various shapes of cavitation 18 may be achieved by the addition of various shapes of matching layers 3 on the inner side of the piezoceramic ring 2 similarly to the cavitation patterns that may be achieved by changing the shape of the vibratable element 2 itself as was illustrated above.

Figure 11:
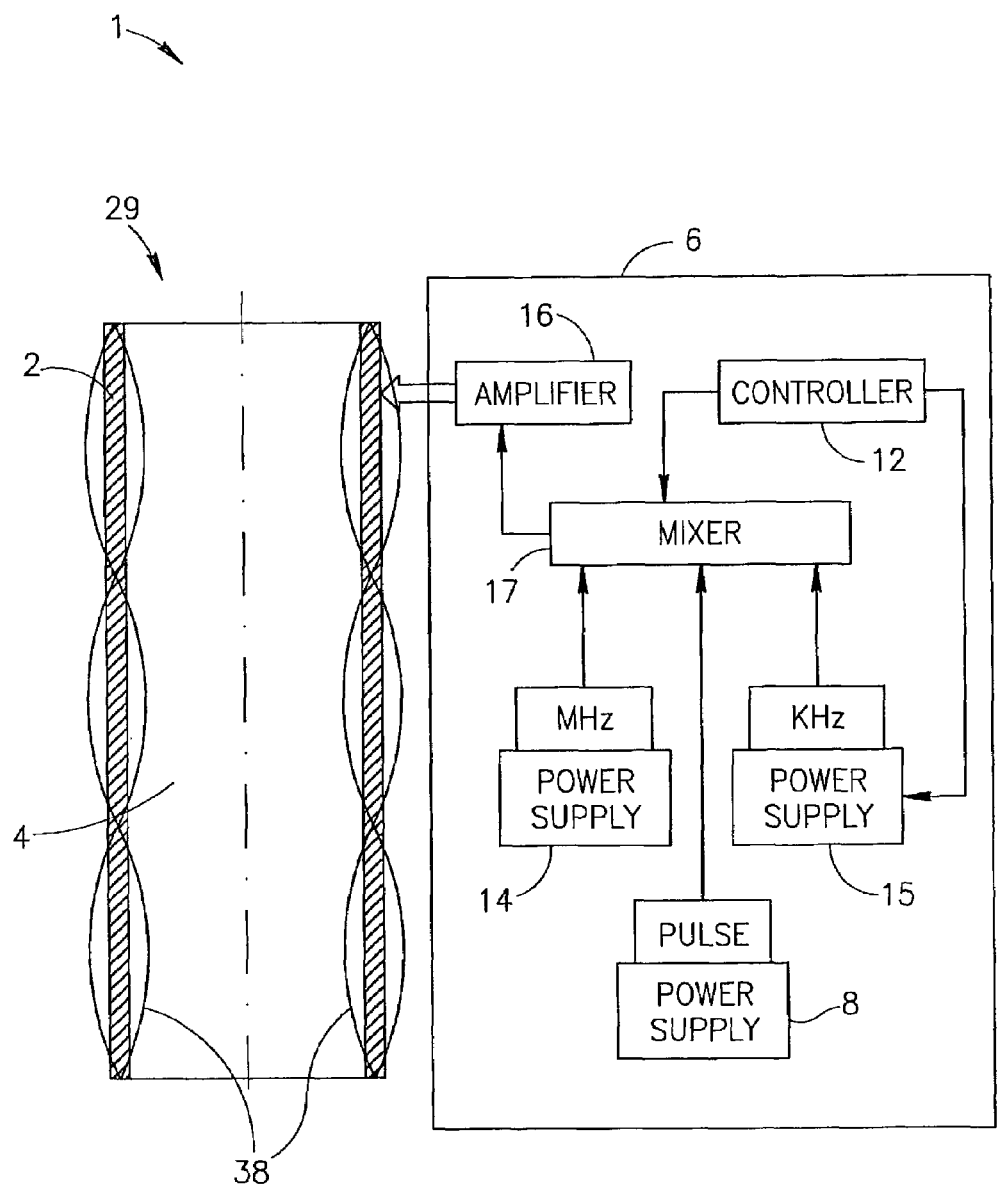
FIG. 11 is a schematic illustration including a block diagram illustration of a sterilization system according to a further embodiment of the present invention, wherein longitudinal and thickness vibrations are applied.

Reference is now made to FIG. 11, which illustrates a diagram of a further embodiment of the sterilization system. In the longitudinal sterilization system waves that are in longitudinal direction to the vibratable element 2 may be supplied. These waves may be supplied in addition to the waves that may be applied through the thickness of the vibratable element 2 in the thickness sterilization system. This may provide a scanning pattern of focused cavitation bubble area 18.

Sterilization system 1 may include container 29 with liquid 4 therein. Container 29 may have an inner or outer vibratable element 2, that may be coated with a conducting material and may be connected to a power supply system 6.

The power supply system 6 may include of the following: a pulse power supply 8, MHz and KHz power suppliers 14 and 15 respectively, a mixer 17, a controller 12 and an amplifier 16. Power supply system 6 may include other parts suitable for supplying electric waves to vibratable element 2.

A pulse power supply 8 may be adapted to supply electric waves having an initial frequency, the MHz power supply 14 may be adapted to supply electric waves at a frequency that may be required for generating thickness waves described in FIG. 4 and the Kilohertz (KHz) power supply 15 may be adapted to supply electric waves at a frequency typically in a range of 50-500 KHz for generating the longitudinal waves. The controller 12 may be adapted to control the MHz power supply so as to achieve the resonance frequency in the thickness mode system. Mixer 17 may be adapted to group the MHz and KHz waves to a combined wave that may enter the vibratable element 2 after amplification by the amplifier 16.

The vibratable element 2 may oscillate in response to the combined electrical input. The MHz power supply 14 may cause thickness waves (not shown) and the KHz power supply 15 may cause longitudinal or bending waves 38. These waves when operating together may provide various shapes of cavitation regions, as will be described hereinbelow. Pulse power supply 8 and controller 12 may operate, similarly as was described for FIG. 4, to supply a combination of KHz and MHz electric waves that may have a frequency which may the frequency resonance of vibratable element 2 and the liquid 4.

Figure 12A:
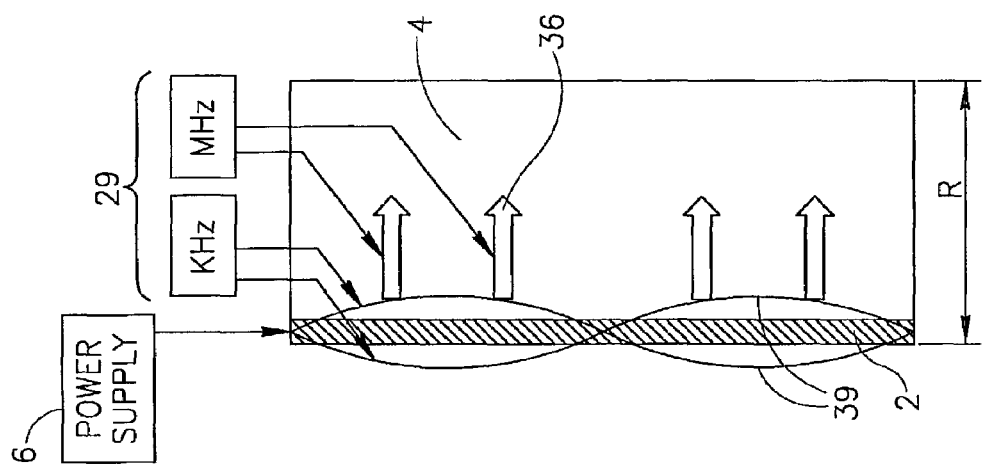
FIGS. 12A-12B are illustrations of first and second mode longitudinal vibration wave patterns and thickness mode wave patterns according to an embodiment of the present invention.
Figure 12B:
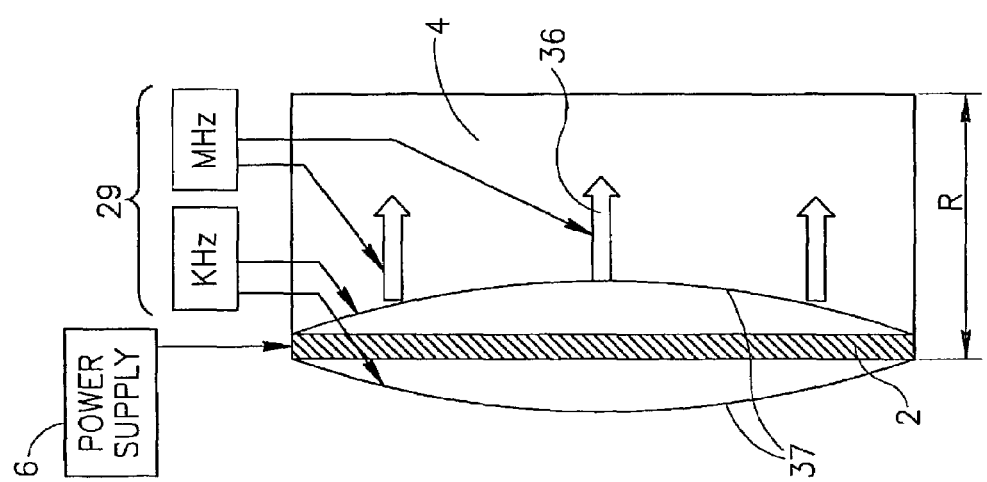

FIGS. 12A and 12B are schematic illustrations of longitudinal vibration wave patterns according to an embodiment of the present invention. Two wave patterns 37 and 39, which will be referred as the first and second mode of the longitudinal vibrations respectively, are presented. In the second mode of vibration, wave pattern 39, the frequency of the waves is double the frequency of the waves in the first mode, wave pattern 37. These wave patterns may be obtained in the vibratable element 2 and in the liquid 4 by a combination of the longitudinal vibrations with the thickness vibrations, for the cylindrical piezoceramic ring 2 configuration of the sterilization system 1 (As is shown in FIGS. 1A-1E). Other wave patterns may be used.

Figure 13A:
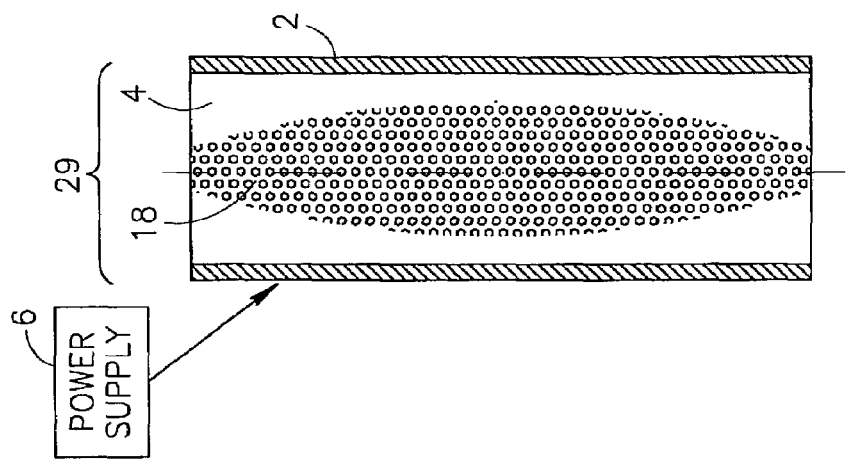
FIGS. 13A-13C are schematic illustrations of produced cavitation patterns in a cylindrical piezoceramic ring when applying the first mode wave pattern of longitudinal vibrations according to an embodiment of the present invention.
Figure 13B:
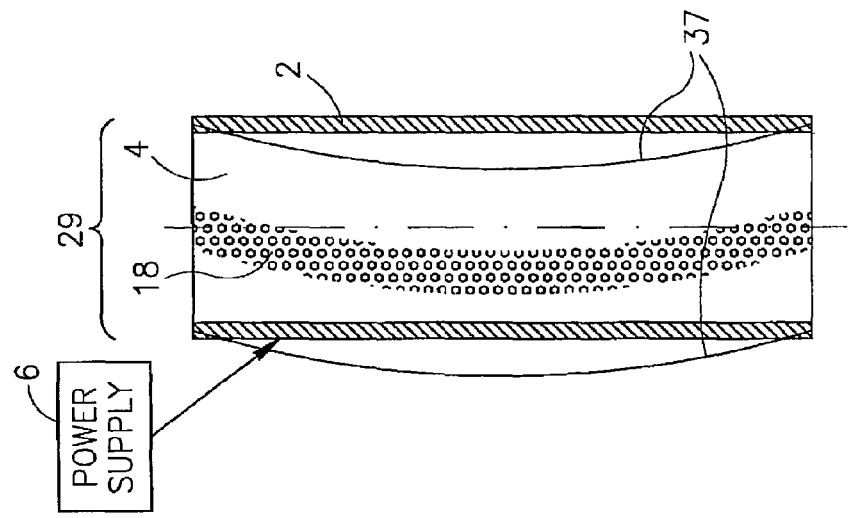
Figure 13C:
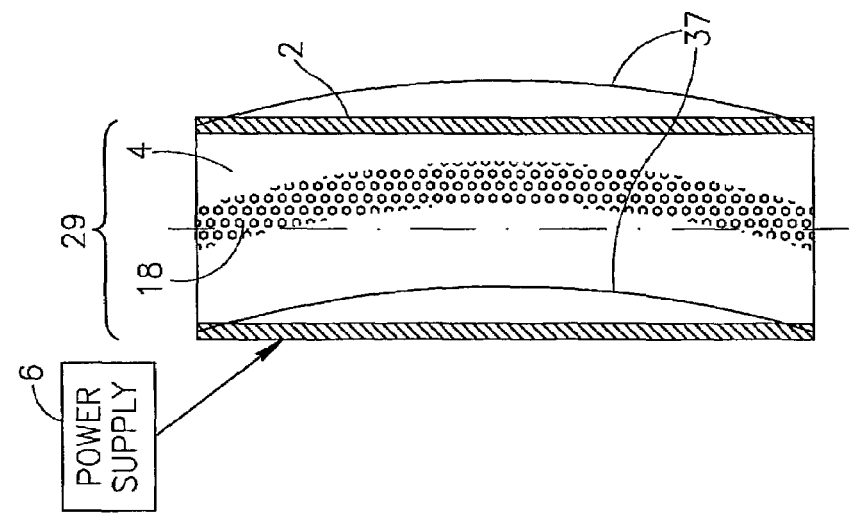

Reference is now made to FIGS. 13A-13C which are schematic illustrations of produced cavitation patterns in a cylindrical piezoceramic ring when applying the first wave pattern of longitudinal vibrations according to an embodiment of the present invention.

FIG. 13 is a longitudinal cross section of container 29 with liquid 4, having a vibratable element 2. A cavitation bubble 18 pattern may be produced as a result of the first mode longitude vibrations 37 that may be applied by the power supply system 6.

In FIG. 13A, the positive amplitude of the first wave pattern 37 and the corresponding cavitation bubbles 18 are illustrated. In FIG. 13B, the negative amplitude of the first wave pattern 37 and the corresponding cavitation bubbles 18 are illustrated. In FIG. 13C the cavitation bubbles 18 may be achieved in a tube having a cylindrical piezoceramic ring 2 by the whole longitudinal vibration wave are illustrated. While applying first mode longitudinal vibration to the thickness mode sterilization system, the a scanning pattern of the focused cavitation area may be achieved.

Figure 14C:
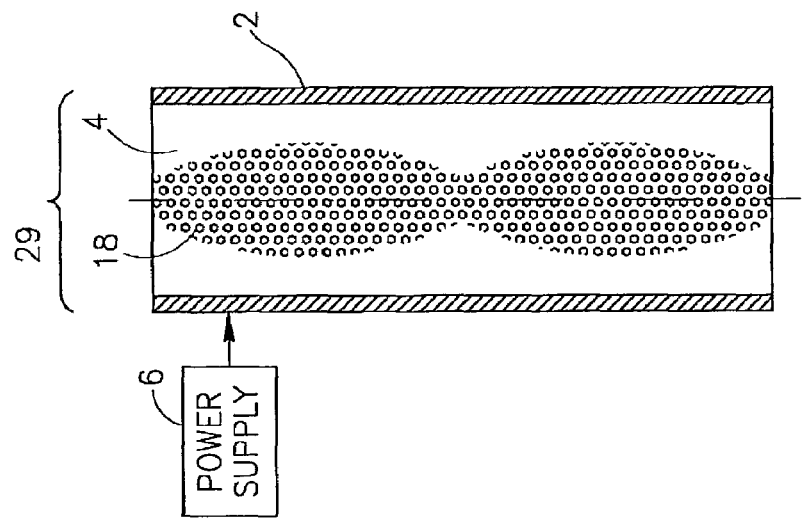
FIGS. 14A-14C are schematic illustrations of produced cavitation patterns in a cylindrical piezoceramic ring when applying the second mode wave pattern of longitudinal vibrations according to an embodiment of the present invention.
Figure 14B:
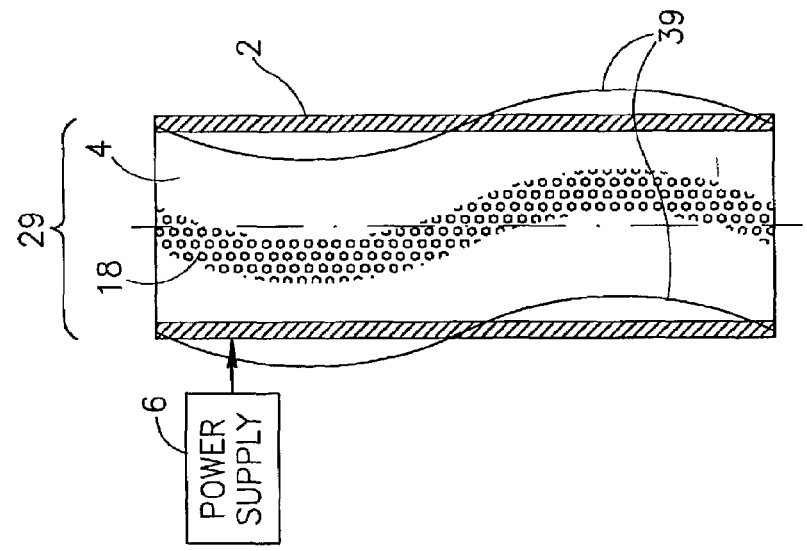
Figure 14A:
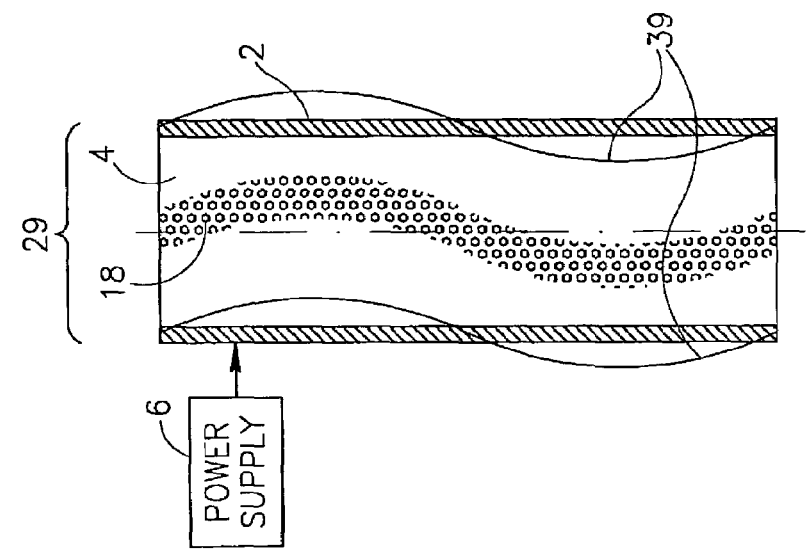

FIGS. 14A-14C are schematic illustrations of produced cavitation patterns in a cylindrical piezoceramic ring when applying the second wave pattern of longitudinal vibrations according to an embodiment of the present invention. Here, similarly to FIG. 13, a cavitation bubble pattern 18 may be produced as a result of the second mode longitudinal vibrations 39.

In FIG. 14A, the positive amplitude of the second wave pattern 39 and the corresponding cavitation bubbles pattern 18 are illustrated. In FIG. 14B, the negative amplitude of the second wave pattern 39 and the corresponding cavitation bubbles pattern 18 are illustrated. In FIG. 14C the cavitation bubbles pattern 18 obtained in tube 30 by the whole longitudinal vibration wave 38 is illustrated. While applying second mode longitudinal vibration to the thickness mode sterilization system, the a scanning pattern of the focused cavitation area may be achieved. Other modes of longitudinal vibration may be used.

Figure 15C:
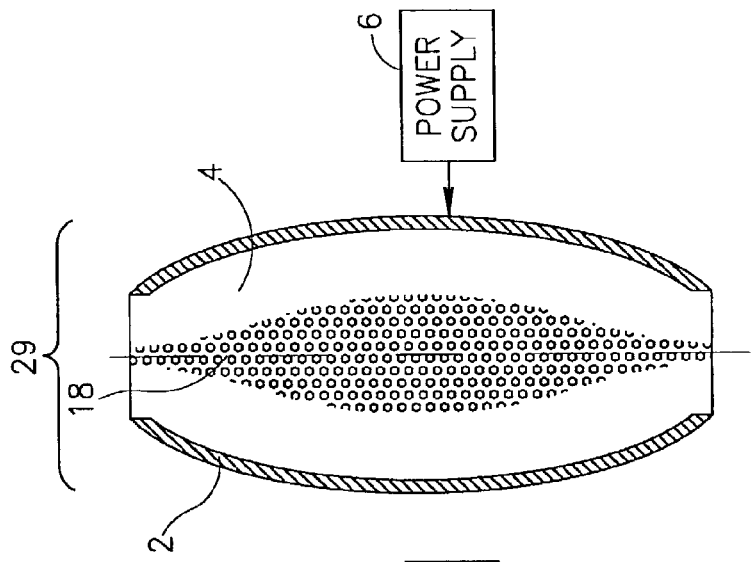
FIGS. 15A-15C are schematic illustrations of produced cavitation patterns in a convex piezoceramic ring when applying the first mode wave pattern of longitudinal vibrations according to an embodiment of the present invention.
Figure 15B:
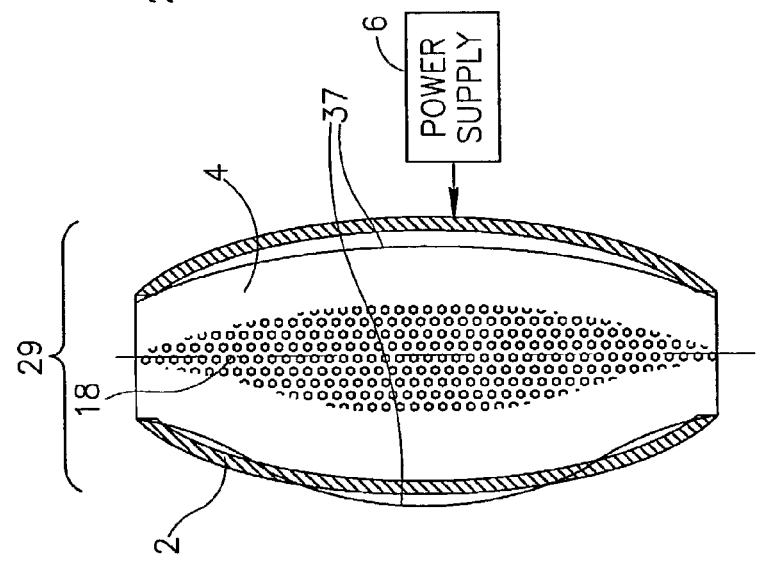
Figure 15A:
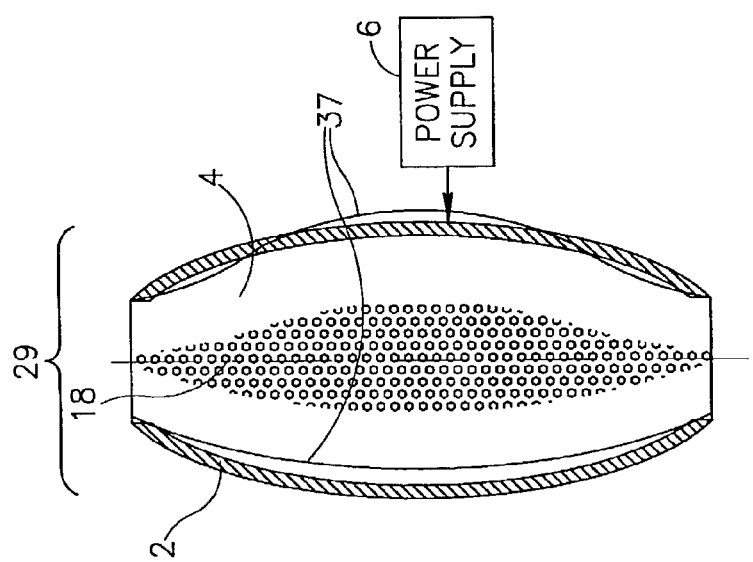

FIGS. 15-20 are schematic illustrations of produced cavitation patterns, that may be producing various shapes of piezoceramic rings and when applying the first wave pattern of longitudinal vibrations, according to an embodiment of the present invention. In FIGS. 15 and 16 the convex piezoceramic ring shape is used, in FIGS. 17 and 18 the concave shape is used and in FIGS. 19 and 20 the tapered shape is used.

Figure 17C:
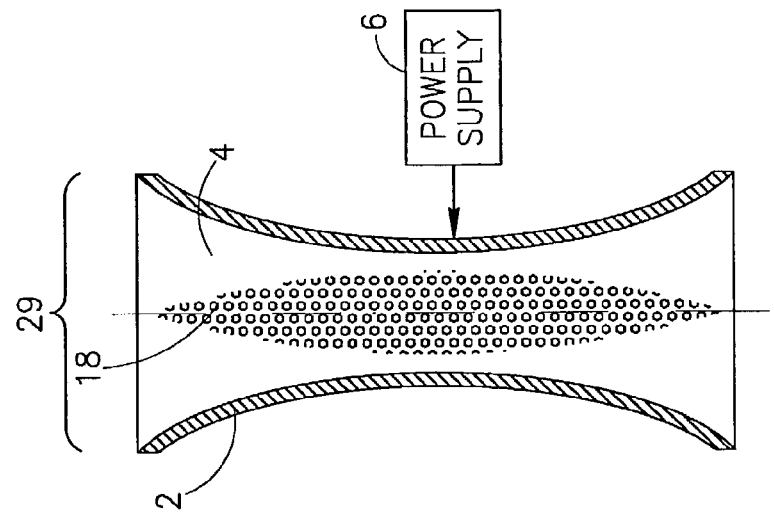
FIGS. 17A-17C are schematic illustrations of produced cavitation patterns in a concave piezoceramic ring when applying the first mode wave pattern of longitudinal vibrations according to an embodiment of the present invention.
Figure 17B:
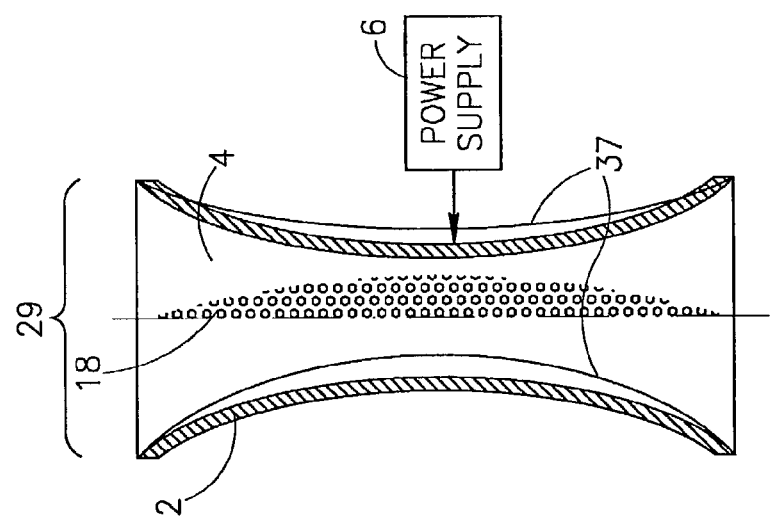
Figure 17A:
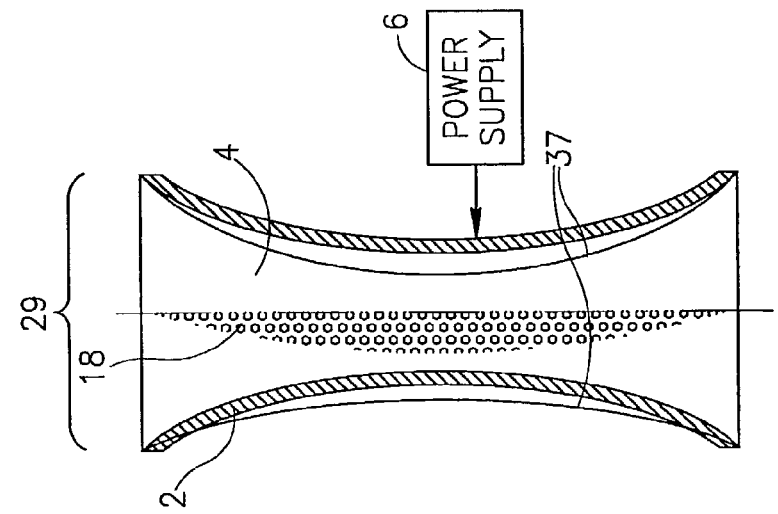
Figure 19C:
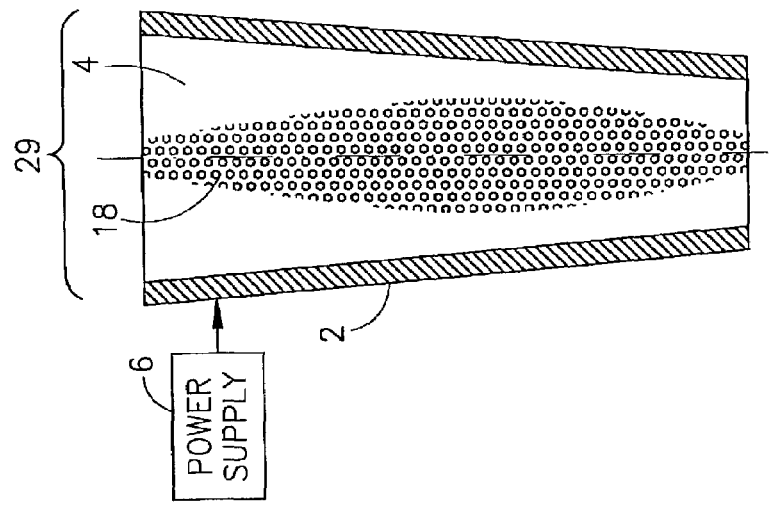
FIGS. 19A-19C are schematic illustrations of produced cavitation patterns in a tapered piezoceramic ring when applying the first mode wave pattern of longitudinal vibrations according to an embodiment of the present invention.
Figure 19B:
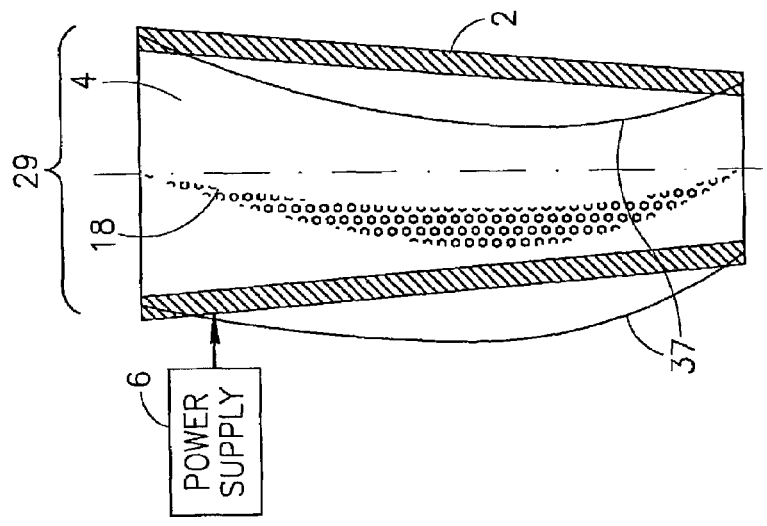
Figure 19A:
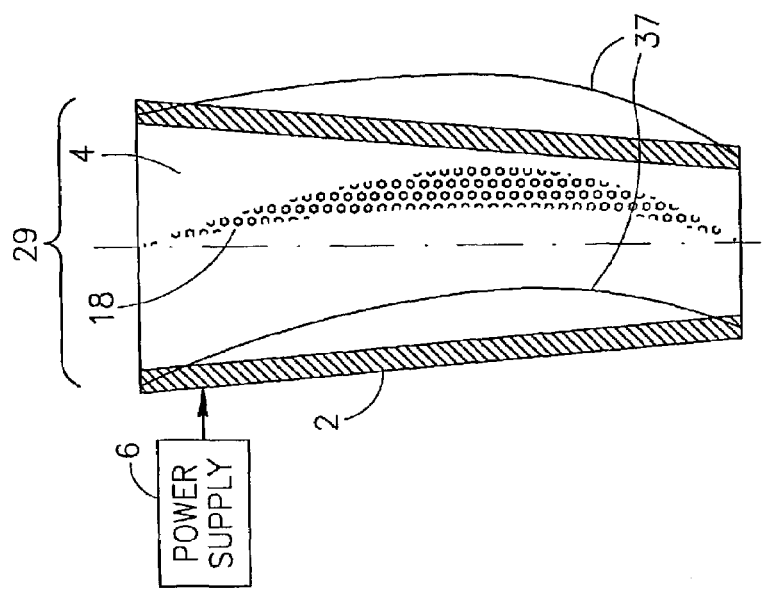

In FIGS. 15, 17 and 19 a cavitation bubble pattern 18 may be produced as a result of the first mode longitude vibrations 37 similarly to FIG. 13.

Figure 18C:
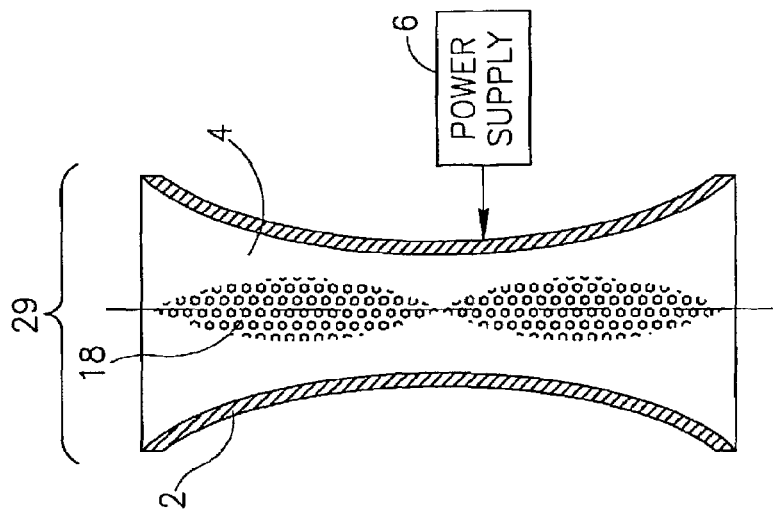
FIGS. 18A-18C are schematic illustrations of produced cavitation patterns in a concave piezoceramic ring when applying the second mode wave pattern of longitudinal vibrations according to an embodiment of the present invention.
Figure 18B:
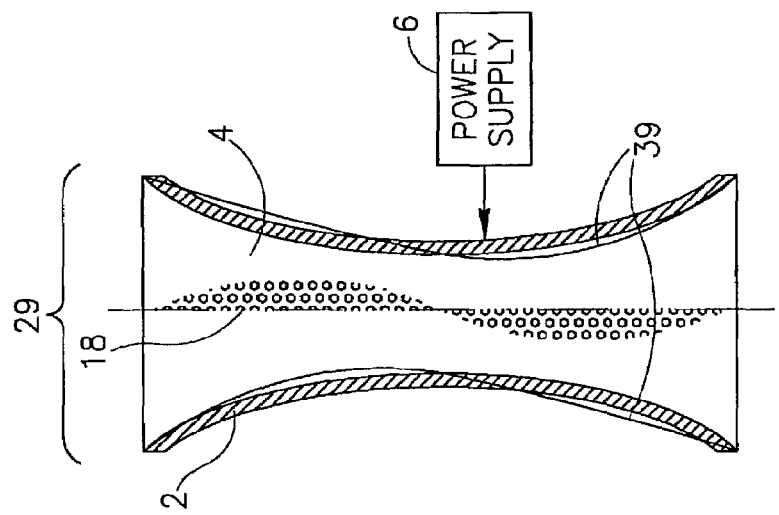
Figure 18A:
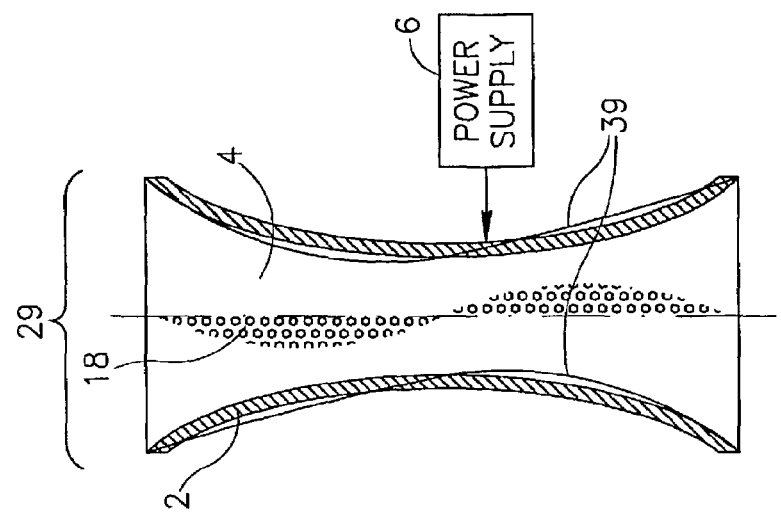
Figure 20C:
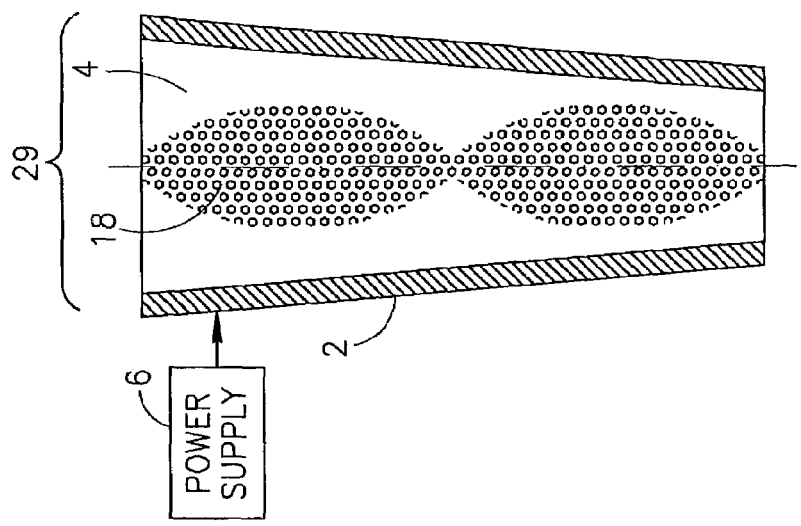
FIGS. 20A-20C are schematic illustrations of produced cavitation patterns in a tapered piezoceramic ring when applying the second mode wave pattern of longitudinal vibrations according to an embodiment of the present invention.
Figure 20B:
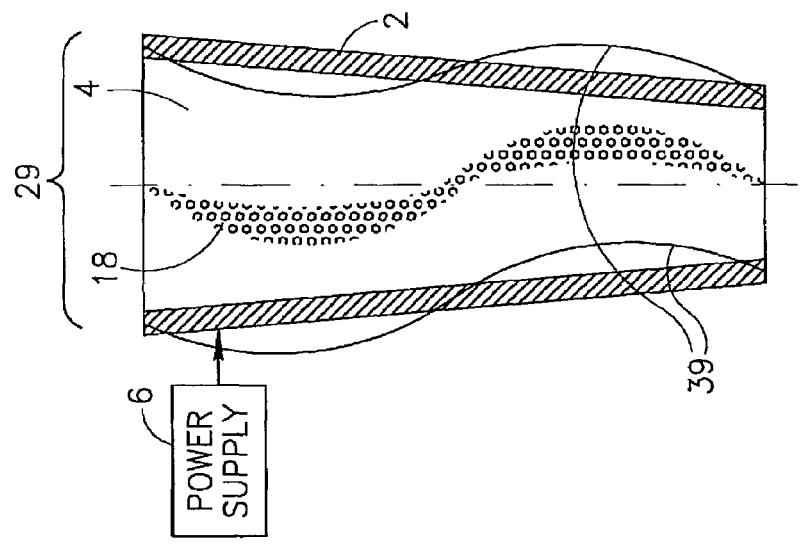
Figure 20A:
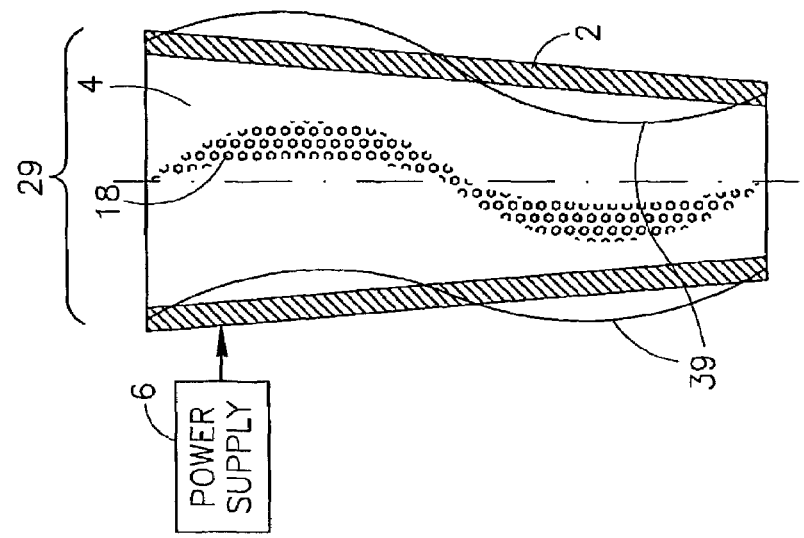

In FIGS. 16,18 and 20 a cavitation bubbles pattern 18 may be produced as a result of the second mode longitude vibrations 39.

Figure 21:
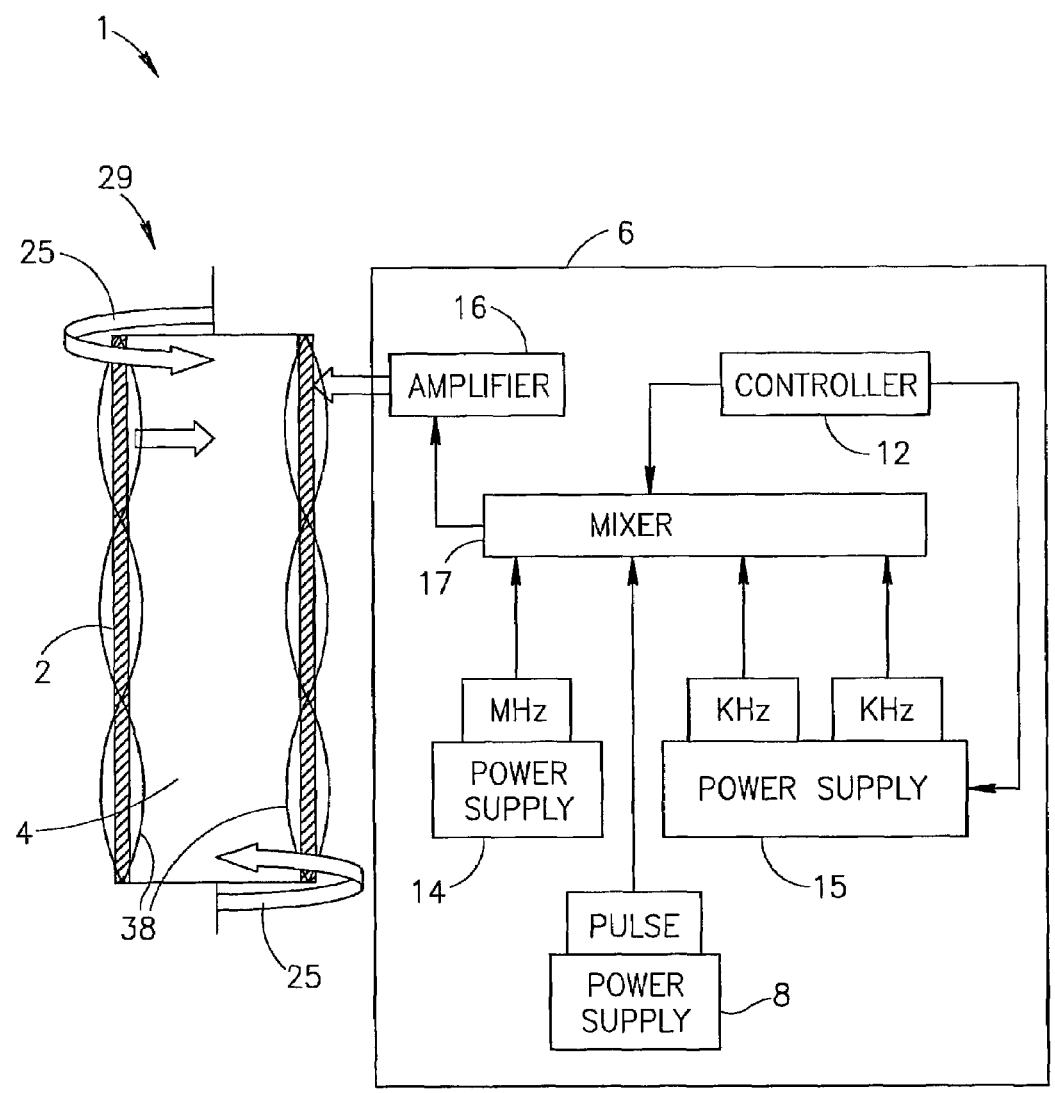
FIG. 21 is a schematic illustration including a block diagram illustration of a sterilization system according to a further embodiment of the present invention, wherein vibrations that cause forces, including torsion forces, to be applied to a liquid.

Reference is now made to FIG. 21 which is a schematic illustration including a block diagram illustration of a sterilization system according to a further embodiment of the present invention, wherein vibrations that causes torsion forces are applied. Waves that cause torsion forces may be applied through the thickness of the piezoceramic ring in addition to the thickness mode vibrations and the longitudinal mode vibrations.

Figure 22:
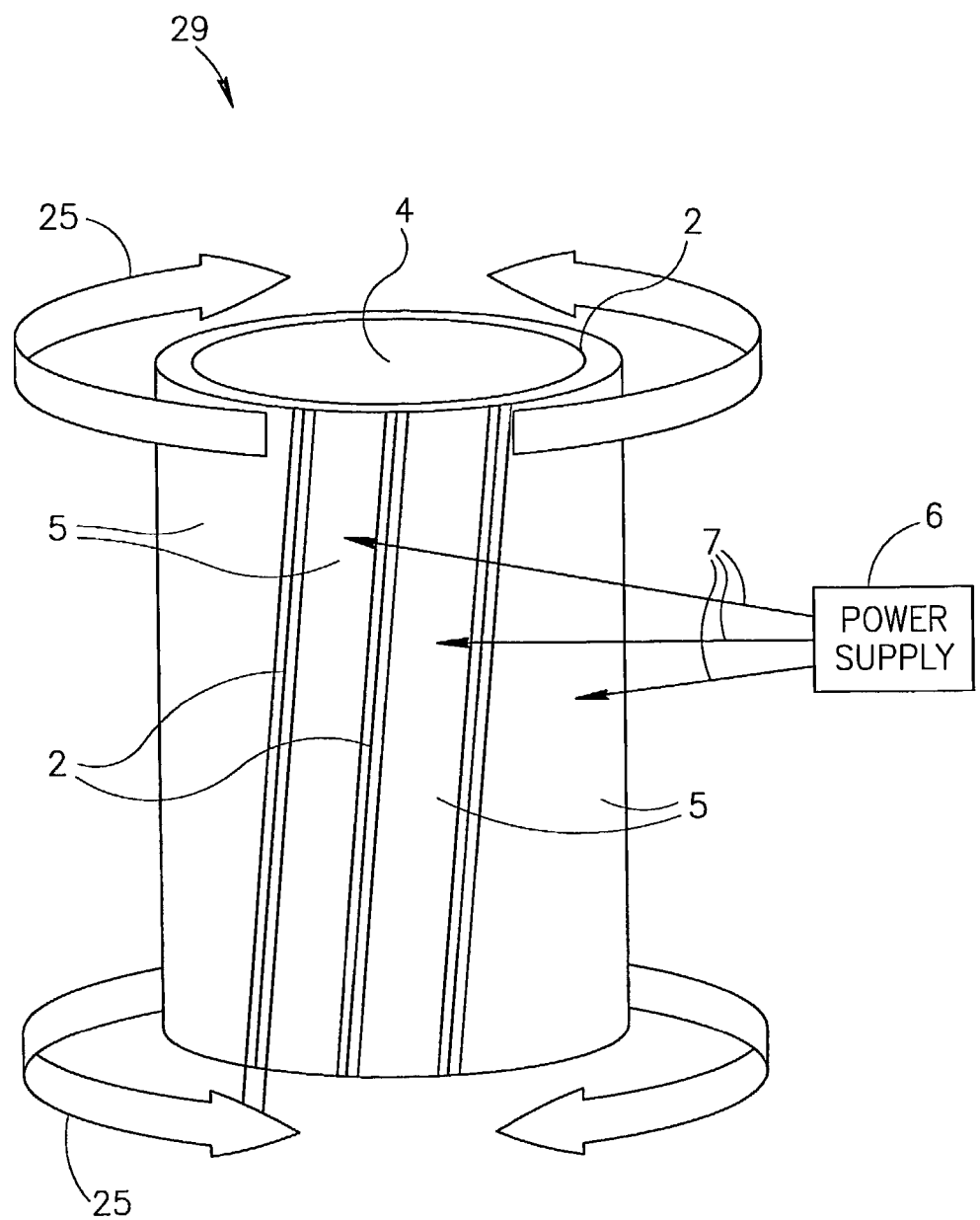
FIG. 22 is illustration of the piezoceramic ring with a conducting layer wherein vibrations that cause torsion forces are applied according to an embodiment of the present invention.
Figure 23A:
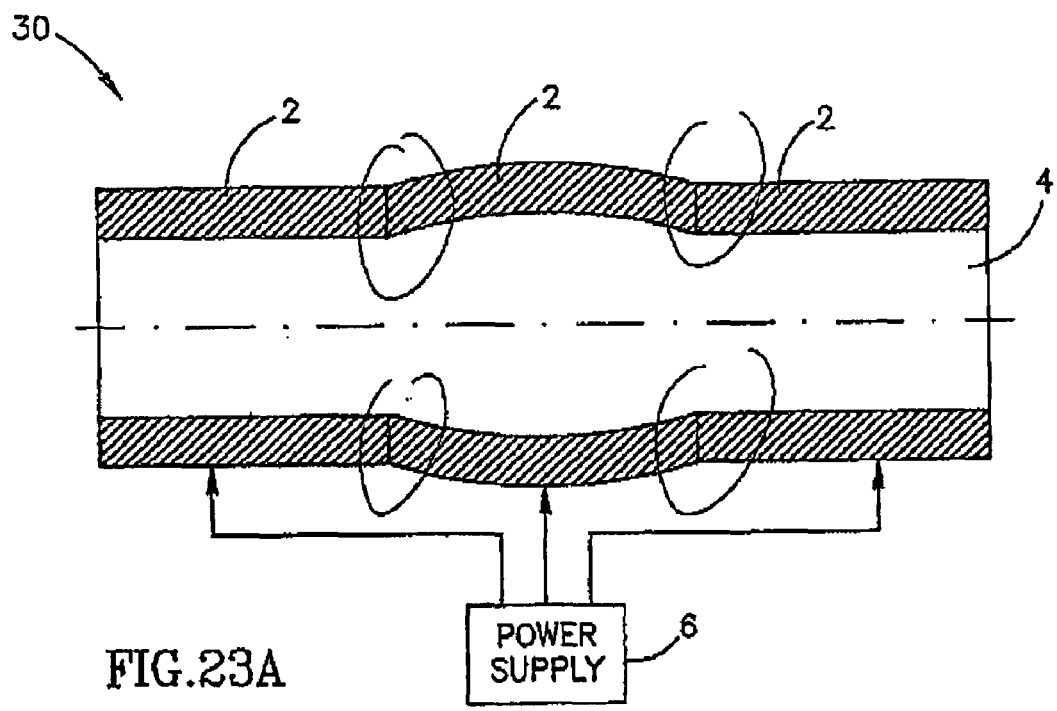
FIGS. 23A-23D illustrate a further embodiment of the sterilization system wherein at least two piezoceramic rings are connected on line.
Figure 23B:
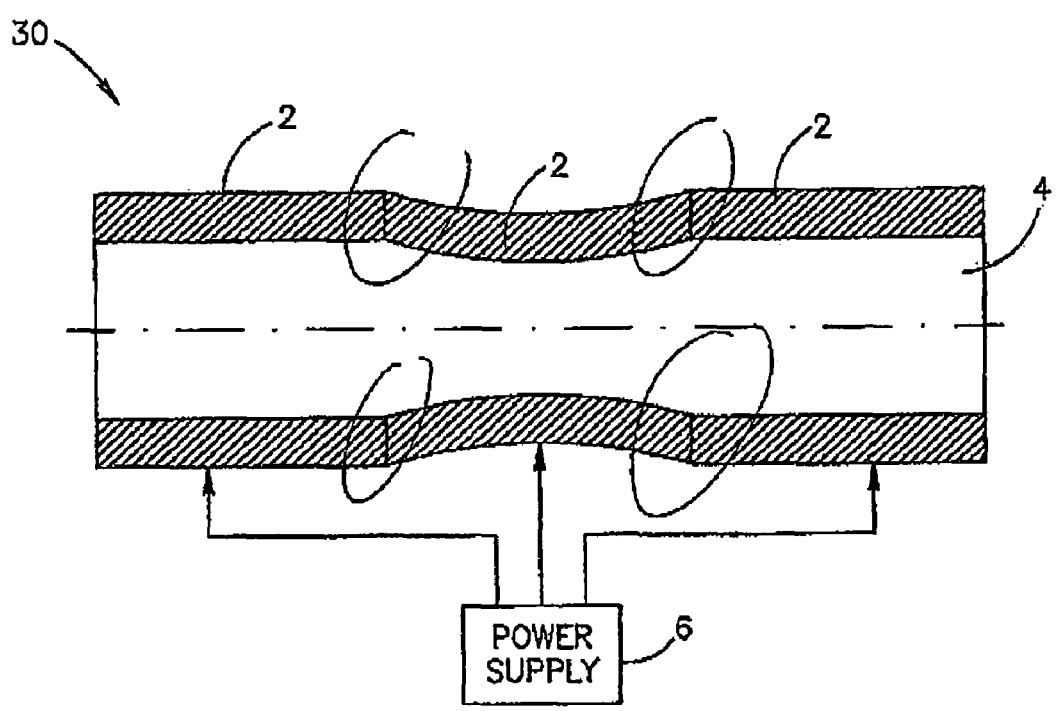
Figure 23C:
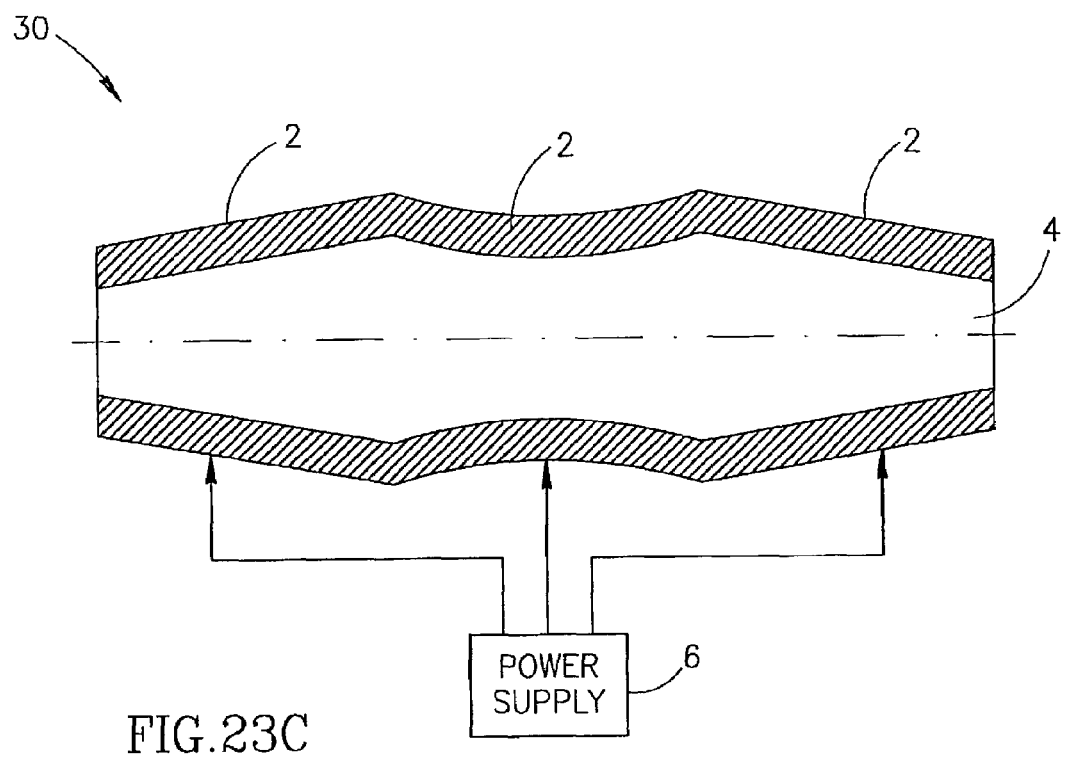
Figure 23D:
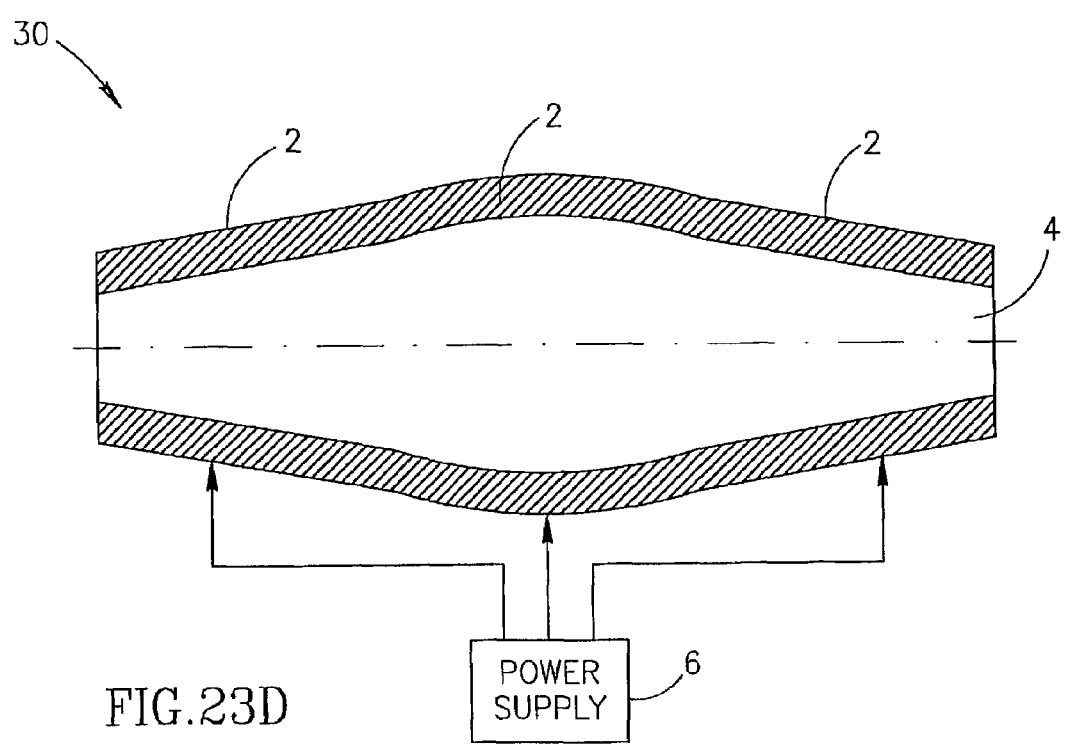

FIG. 22 is an illustration of the piezoceramic ring wherein vibrations that causes torsion forces are applied according to an embodiment of the present invention. In order to achieve torsion forces the conducting layer 5, coated on the vibratable element 2 may include one or more portions of non-conducting material as illustrated. The non-conducting material may be applied to at least a portion of the inner surface and/or outer surface of the vibratable element 2. This may be achieved, for example, by cutting the conducting layer and exposing strips of non-conducting piezoceramic material 2, other method for including non-conducting material may be used. The torsion forces that may thus be achieved are depicted by arrow 25. Since the conducting layer may have portions of non-conducting material, it may be desirable to have the electric wires 7 in contact with each section of the conducting material 5, such that power may be supplied to the whole vibratable element 2.

The torsion forces may be achieved in the cylindrical piezoceramic ring as illustrated in FIG. 22 as well as in other shapes of piezoceramic rings 2, such as, for example, convex, concave and tapered piezoceramic rings.

FIGS. 23A-23D illustrates a further embodiment of the sterilization system wherein at least two piezoceramic rings are connected on line. The piezoceramic rings 2 may have various shapes and may be connected to the thickness sterilization system as described in FIG. 4 as well as to the longitudinal and torsion sterilization system as described in FIG. 11 and 21, respectively. In some embodiment of the present invention the on-line vibratable elements 2 may be connected together to the same power supply system as illustrated, alternatively, one or more vibratable elements 2 may be connected to a different power supply system (not shown). The piezoceramic rings 2 may all be constructed from the same piezoceramic material or each ring may be constructed from a different piezoceramic material. By connecting various shapes of piezoceramic rings 2 along the tubes a selective sterilization may be achieved since, as was illustrated hereinabove the piezoceramic ring shape influence the cavitation pattern.

Figure 24A:
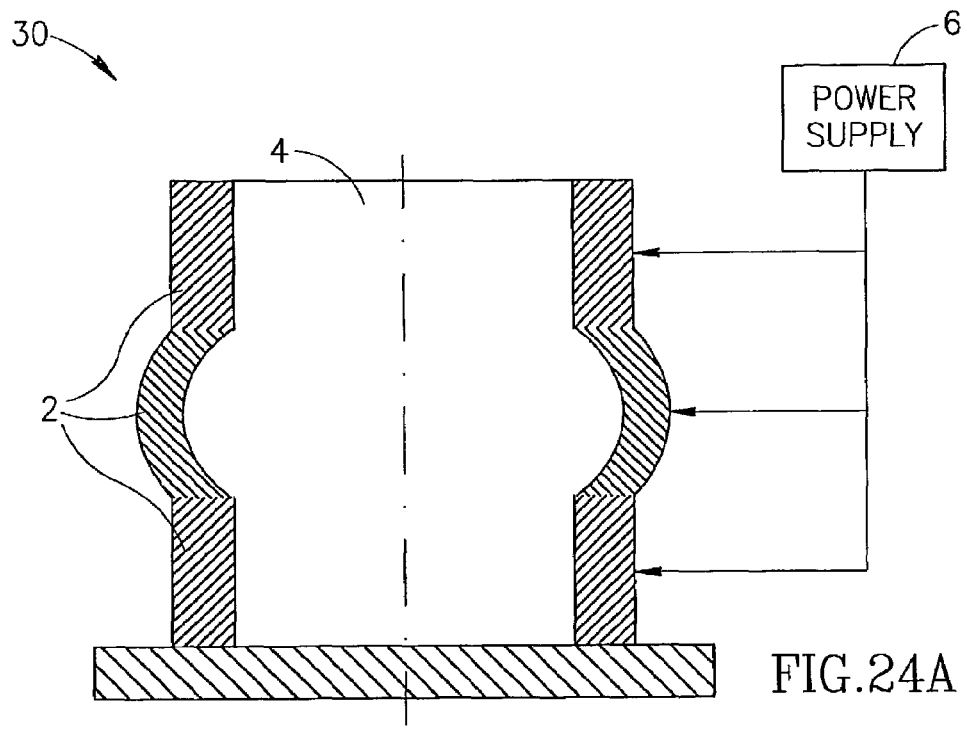
FIGS. 24A-24B illustrate a further embodiment of the sterilization system wherein at least two piezoceramic rings are connected on line in a vessel.
Figure 24B:
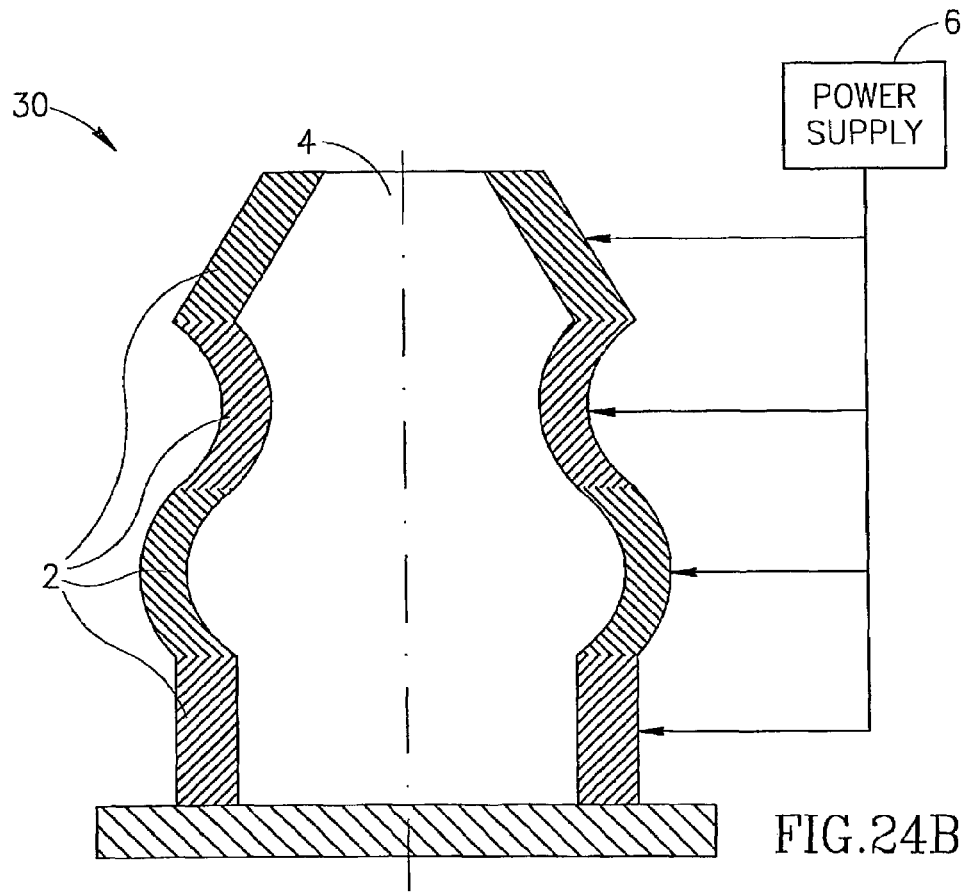

FIGS. 24A-24B illustrate a further embodiment of the sterilization system wherein at least two piezoceramic rings are connected on line in a vessel. The vibratable element 2 may be of various shapes as illustrated in FIG. 24A and 24B and may be connected to the thickness sterilization system as described in FIG. 4 as well as to the longitudinal or torsion sterilization systems as described in FIG. 11 and 21 respectively. All the on-line vibratable elements 2 or vibratable element's portions may be connected together to the same power supply system 6. Alternatively, each vibratable element or portion 2 may be connected separately to a different power supply system 6. Vibratable element 2 may all be constructed from the same piezoceramic material or each ring or portion may be constructed from a different piezoceramic material or for a non-piezoceramic material. Different sterilization modes may be applied to each vibratable element 2 or to each portion.

Figure 25A:
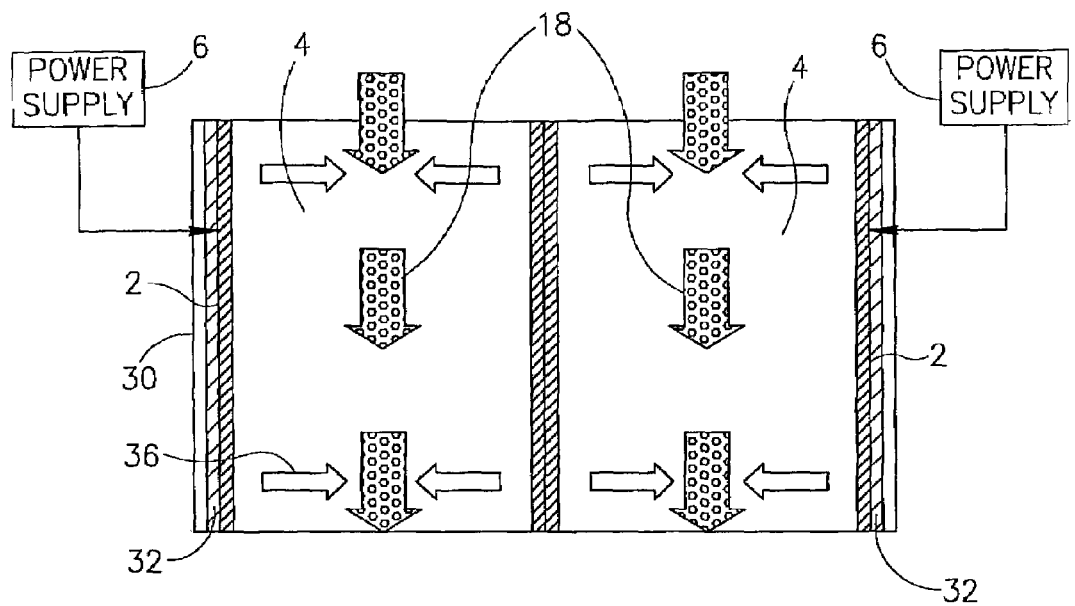
FIGS. 25A-25B illustrate a further embodiment of the sterilization system wherein several piezoceramic rings are connected in parallel.
Figure 25B:
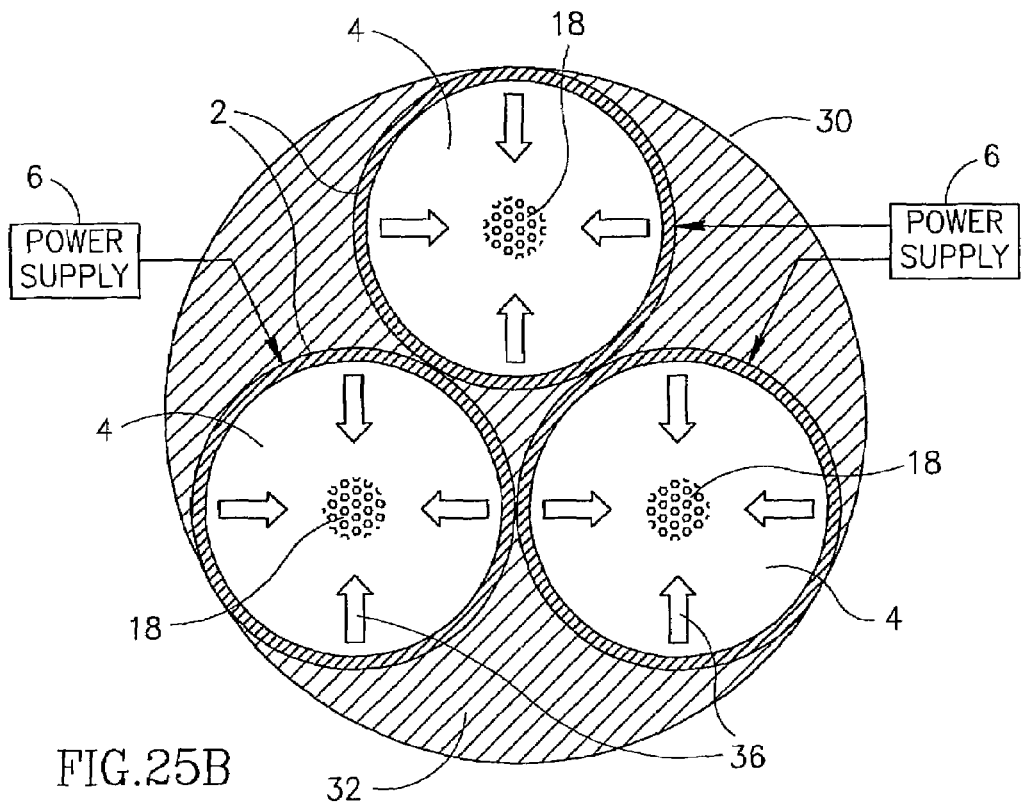

FIGS. 25A-25B illustrate further embodiment of the sterilization system wherein several piezoceramic rings are parallely connected. FIG. 25A illustrates a vertical cross section of tube 30 including vibratable elements 2 wherein each tube may be separately connected to power supply system 6. The void 32 between tube 30 and the vibratable element 2 may be filled with a material such as rubber, plastic, silicone or cork or any other suitable material. Tube 30 may be made of rubber, plastic, silicone, metal or any other suitable material. A thickness, longitudinal or torsion sterilization system may be operated. All the parallel vibratable elements 2 may be connected together to the same power supply system 6, alternatively, one or more vibratable element 2 may be connected to a different power supply system 6.

Tube 30 may include piezoceramic material having cavities thus creating small tubes wherein liquid can flow. This cavities may have any shape described above or any other suitable shape. The cavities may have a diameter range of preferably 0.1-1 micron, other dimension may also be used.

The power supply system may be connected to the tube which may be coated with a conducting layer.

Figure 26A:
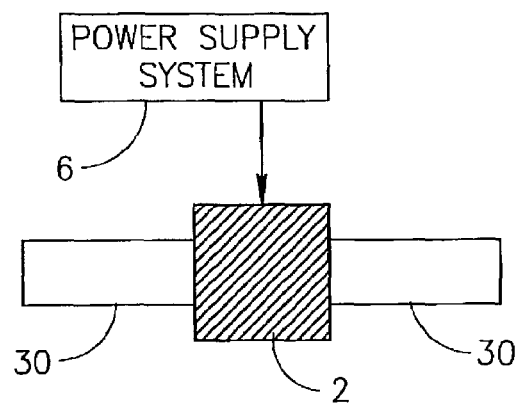
FIGS. 26A-26C illustrate a further embodiment of the invention wherein sterilization system is placed at the connection between online tubes.
Figure 26B:
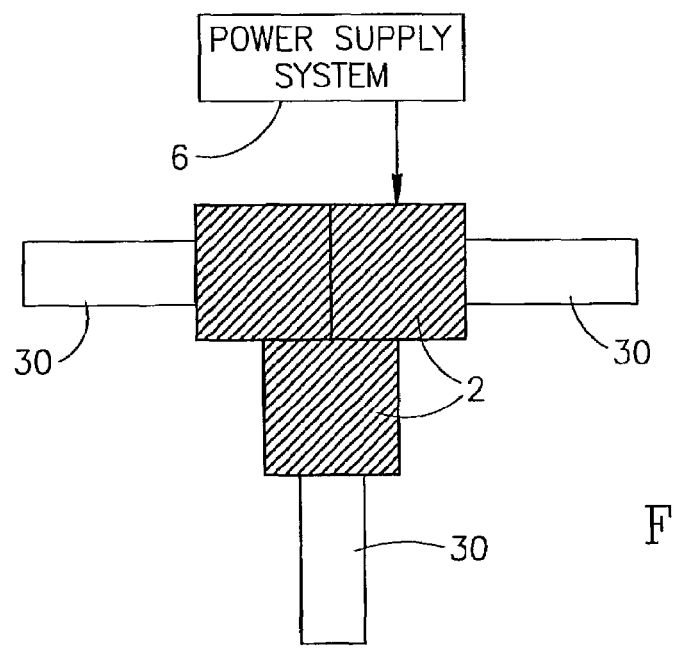
Figure 26C:
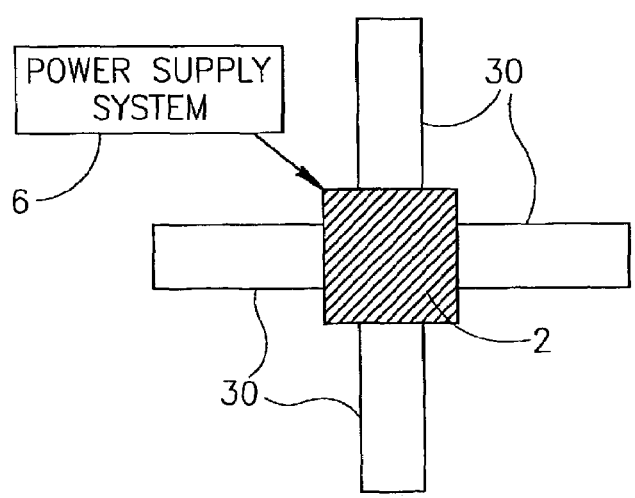

FIGS. 26A-26C illustrate a further embodiment of the invention wherein sterilization system may be placed at the connection between tubes 30. In FIGS. 26A, 26B and 26C sterilization system 1 including vibratable element or elements 2 may be placed at the connection of two tubes, three tubes and four tubes respectively. Vibratable element 2 may have any shape discussed above or any other suitable shape. The vibratable element 2 may be operated according to any of the modes discussed hereinabove.

Figure 27:
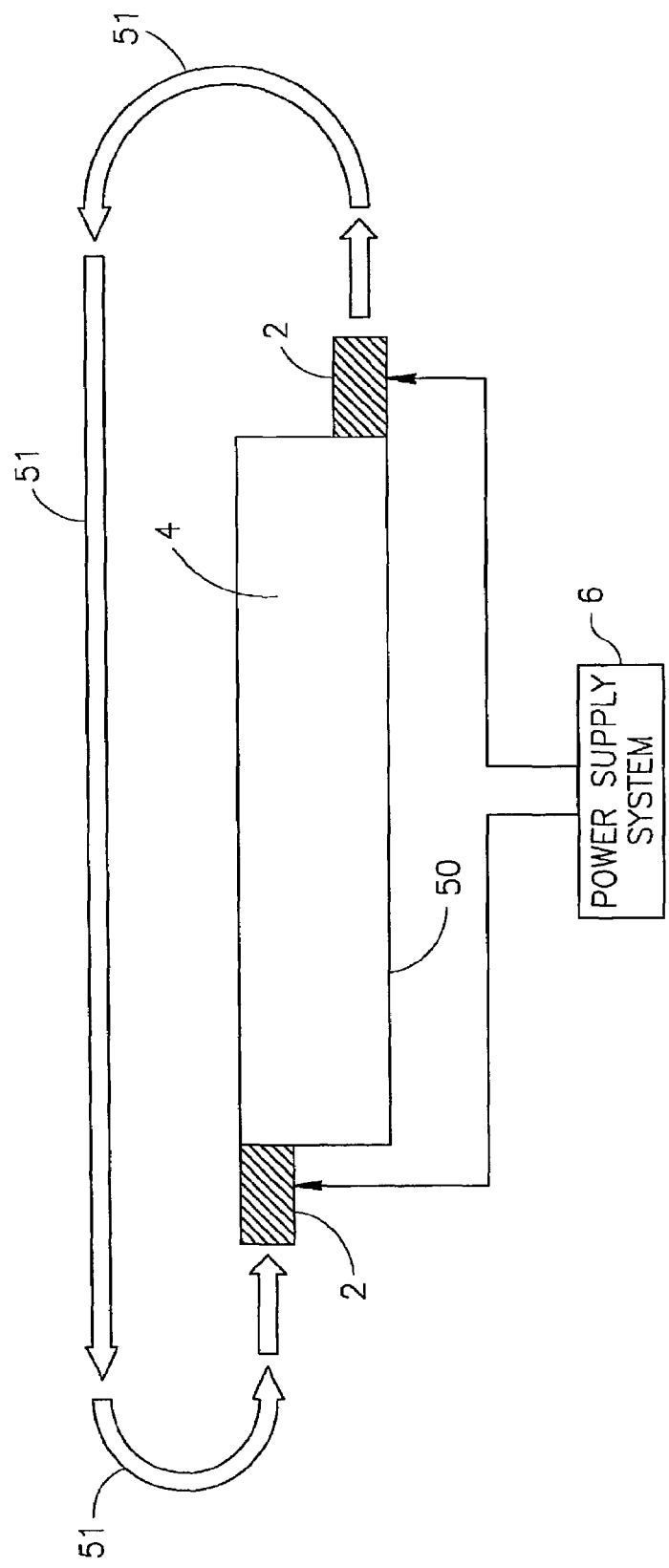
FIG. 27 illustrates a further embodiment of the invention wherein the sterilization system is placed at the entrance and exit of a liquid reservoir.

FIG. 27 illustrates a further embodiment of the invention wherein the sterilization system may be placed at the entrance and exit of a liquid reservoir. Liquid reservoir 50 contains liquid that may be circulating through the sterilization system as depicted by arrows 51. The cavitation created by the sterilization system may destroy bacteria, protozoa and larvae in the liquid as well as other particles existing in the liquid. Vibratable element 2 may have any shape discussed above or any other suitable shape. The vibratable element 2 may be operated according to any of the modes discussed hereinabove.

Figure 28A:
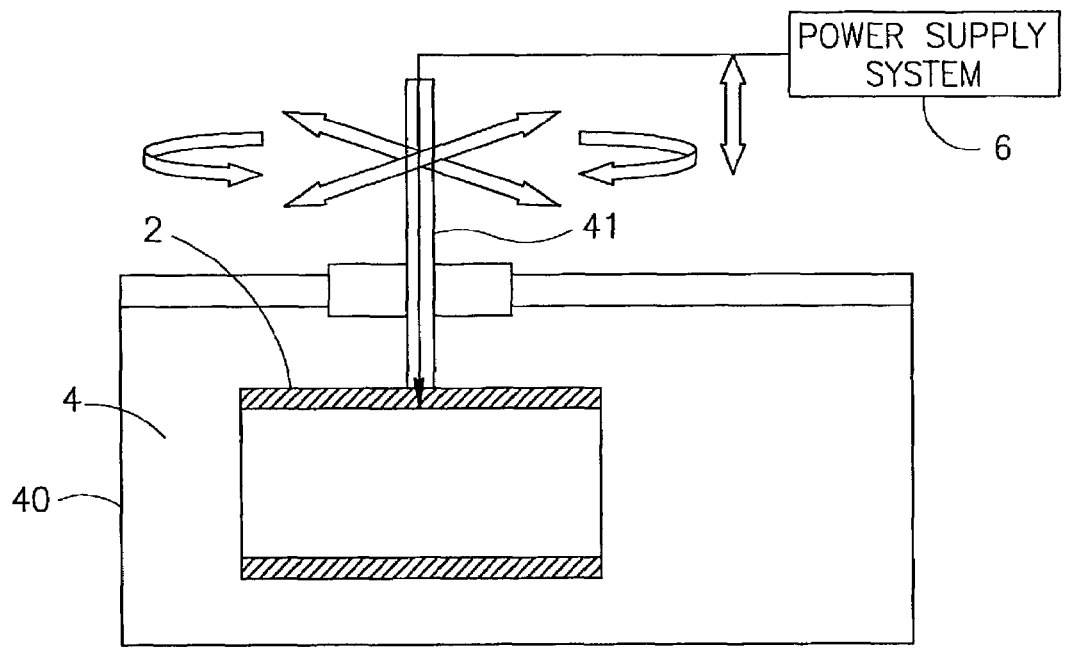
FIGS. 28A-28B illustrate a further embodiment of the sterilization system wherein the piezoceramic ring is movable.
Figure 28B:
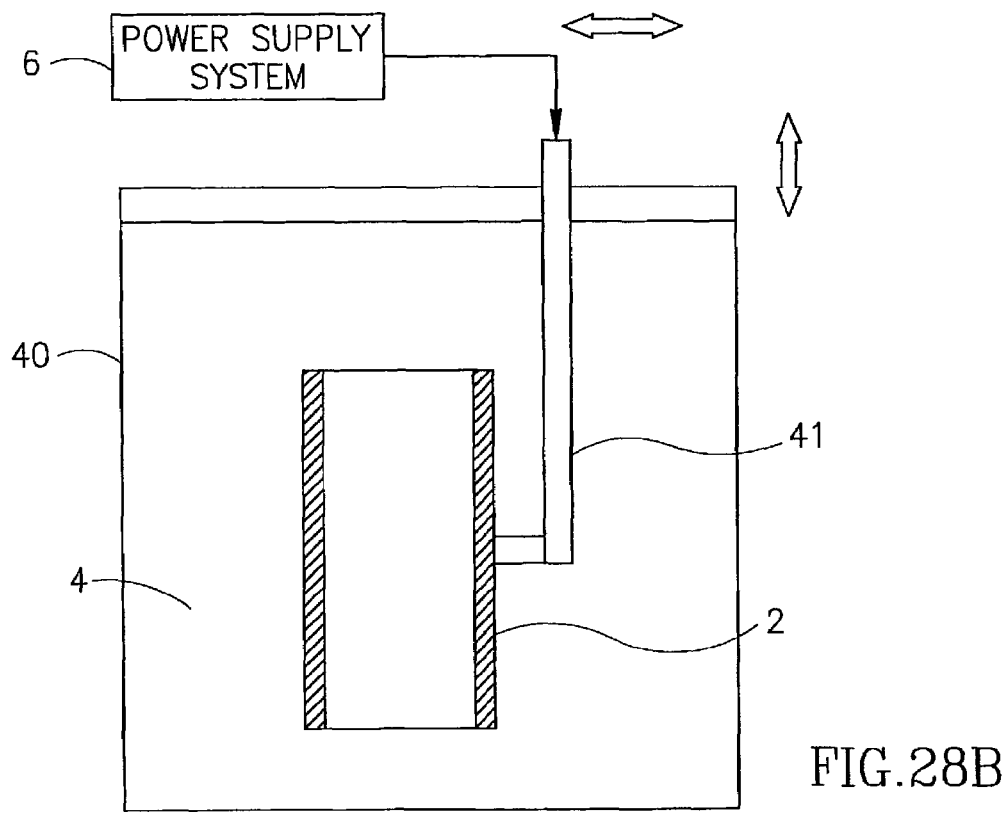

FIGS. 28A-28B illustrate a further embodiment of the sterilization system wherein the vibratable element may be movable. Vibratable element 2 may be placed inside a reservoir 40. The reservoir 40 may contain liquid 4, connected on the outer side to a bar 41, that may emerge from the liquid reservoir. Bar 41 may be connected to a device that may allow its moving on the horizontal and/or vertical axis thus the vibratable element 2 may move inside liquid reservoir 40. The maneuverability of the vibratable element 2 may allow the sterilization of all the liquid 4 in the reservoir 40. The vibratable element 2 may be connected to the power supply system 6 through the bar 41. FIGS. 28A illustrates an embodiment wherein the vibratable element 2 may be parallel to the horizontal axis while FIG. 28B illustrates an embodiment wherein the vibratable element 2 is perpendicular to the horizontal axis. Vibratable element 2 may have any shape discussed above or any other suitable shape. The vibratable element 2 may be operated according to any of the modes discussed hereinabove.

Figure 29:
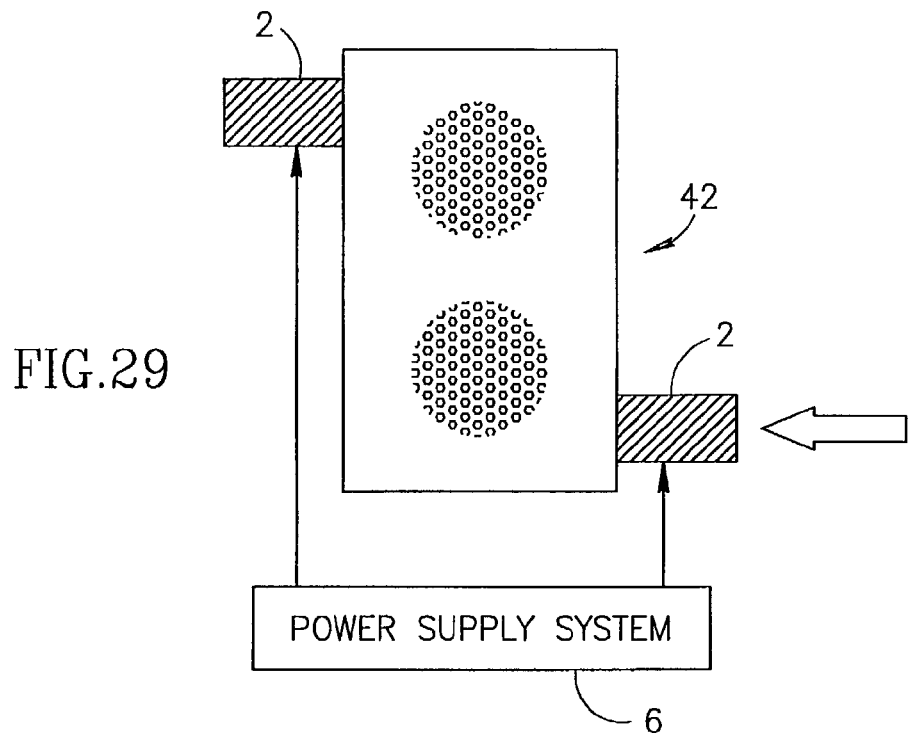
FIG. 29 illustrates a further embodiment of the sterilization system wherein the sterilization system is placed at the entrance and exit of a liquid pump.

FIG. 29 illustrates further embodiment of the invention wherein vibratable element 2 of sterilization system 1 are connected at the entrance and exit of a liquid pump 42 for the sterilization of the pumped liquid. Vibratable element 2 may have any shape discussed above or any other suitable shape. The vibratable element 2 may be operated according to any of the modes discussed hereinabove.

Figure 30:
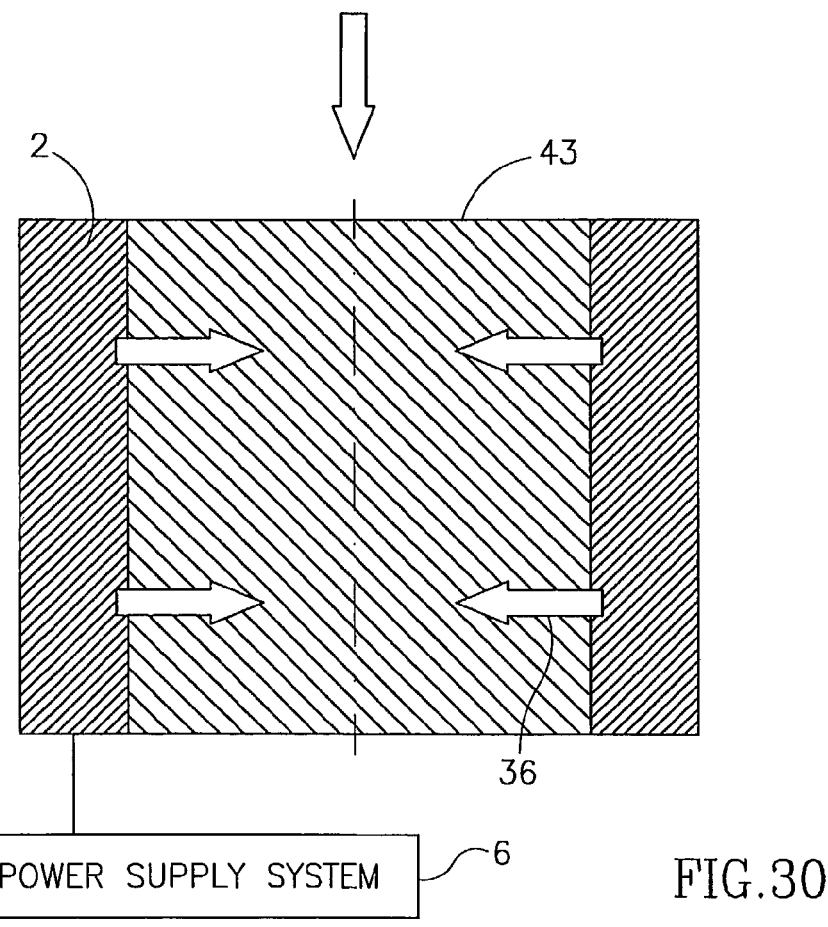
FIGS. 30 illustrates a further embodiment of the sterilization system wherein the piezoceramic ring is places around a filter for liquids.

FIG. 30 illustrates further embodiment of the invention wherein the vibratable element 2 of sterilization system 1 is placed on the outer side of a commercially available liquid filter 43 for the sterilization of the liquid while filtering through the filter. In this case, liquid sterilization and filter cleaning may be performed substantially simultaneously. The vibration of the filter, for example by the piezoceramic element, may be adapted to prevent bio-films formation in the filtering system. Any shape of piezoceramic of vibratable elements discussed above may be used. Vibratable element 2 may have any shape discussed above or any other suitable shape. The vibratable element 2 may be operated according to any of the modes discussed hereinabove.

Figure 33:
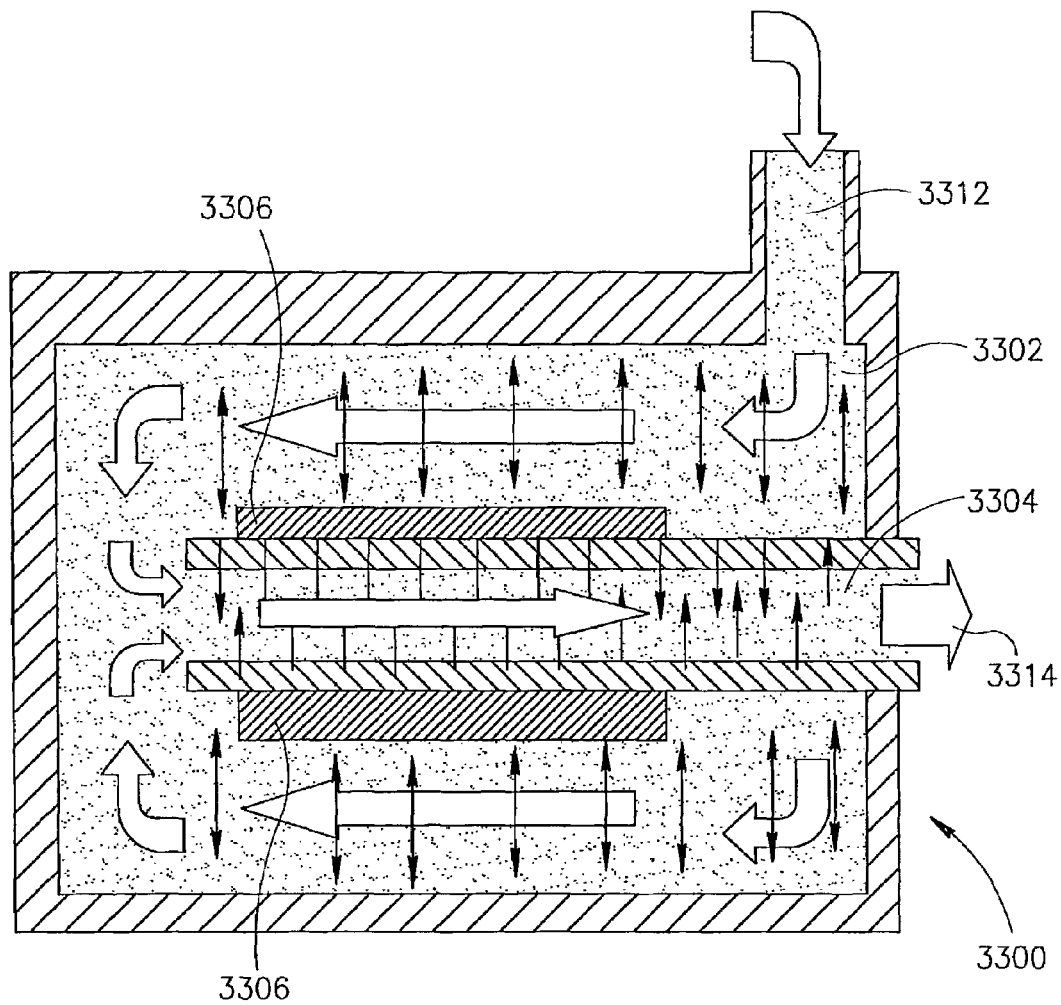
FIG. 33 is a block diagram illustration of a liquid sterilization chamber according to an embodiment of the preset invention.

Reference is made now to FIG. 33, which is a diagrammatic illustration (cross section) of a sterilization chamber in accordance with an embodiment of the present invention. The sterilization chamber 3300 may be adapted to contain a liquid such as water or any other liquid to be treated. The container may be cylindrically shaped, or may be of any other shape. The chamber 3300 may include an outer section 3302 and an inner section 3004. The inner section 3304 and outer sections 3302 may also be cylindrically shaped. For convenience purposes, the liquid within the inner tube 3304 will be referred to as "volume B" and the liquid outside the inner tube 3304 will be referred to as "volume A". The chamber 3300 may further include a vibrating or vibratable element 3306. In some embodiments of the present invention, such as the one shown in FIG. 33, two or more vibrating or vibratable elements 3306 may be used. The vibratable elements 3306 may be constructed according to any of the vibratable elements described above. The vibratable elements 3306 may be attached to either an inner or outer wall of the inner section 3304. In this configuration, the location of the vibratable elements 3306 with respect to volume B may correspond to the configuration described in FIG. 1B, i.e. the vibratable element 3306 is attached to the outer portion of the inner section 3304. However, in other embodiments, the vibratable elements 3306 may be attached to the interior surface of the inner tube 3304. The chamber may also include matching layers (not shown) located and operated in accordance with any of the discussions above.

The chamber may be connected to a power supply and signal generator. The power supply and signal generator may be operatively connected to the vibratable elements. The power supply and signal generator may be constructed in accordance with any of the configurations described above.

A liquid may enter the chamber 3300 through an opening 3312 from an outer source (not shown) to the portion labeled volume A, on either side of the outer section 3302, where the vibratable elements 3306 may be operated as described hereinabove, thereby causing acoustic vibrational oscillations in the liquid. Vibrations from the element 3306 in the outer direction may be reflected from the chamber's wall and may create standing acoustical pressure waves. This may initiate at least a partial liquid sterilization. The oscillation frequency of the vibratable elements 3306 element may be selected, such that the oscillation of the vibratable elements 3306 may cause standing waves in the liquid.

The liquid may proceed into the inner section 3304, labeled volume B, initiation focused acoustic pressure waves as described hereinabove with reference to FIG. 1B. Vibratable elements 3306 may also produce standing waves, possibly simultaneously affecting the liquid in volume A as well as the liquid in volume B, and further sterilizing the liquid to provide a substantially sterilized liquid. The liquid may leave the chamber 3300 through an opening 3314 at the end of the inner section 3304. In this embodiment a single vibratable element 3306 may provide vibrational acoustic waves both in inner and outer directions, this may allow higher affectivity of the sterilization system for example by enhancing the volume of liquid to be sterilized using a single vibratable elements. According to other embodiments multiple may be used (as is shown in FIGS. 26A-26C) this may be suitable where substantially large volumes of water are to be sterilized. Other benefits may exist. Vibratable element 2 may have any shape discussed above or any other suitable shape. The vibratable element 2 may be operated according to any of the modes discussed hereinabove.

EXPERIMENTAL RESULTS

An experimental system was built from a 12 mm diameter cylindrical ring of a piezoceramic material PZT-4 with a thickness of 2 mm and a length of 20 mm. Water was flowing through the ring at a capacity of 1 cm/sec. The water contained an initial microbial concentration of bacteria per volume. The ring was connected to a power supply system as described in FIG. 4 or to a power supply system as described in FIG. 11 or FIG. 21. A microbial test was conducted before and after operation of the sterilization system.

The first microbial test was conducted by AminoLab Laboratory an officially recognized laboratory by Ministry of Agriculture, in Israel, according to the "Standard Methods for the Examination of Water and Wastewater" using the pour plate technique.

FIG. 31 set forth the experimental results for the experimental system and method described above. Six samples—M02524, M02525, M0526, M0527, M0528 and M0529 were detected. Sample M02524 is the control sample contains untreated examined water with initial bacterial count of $9.8 \times 10^4$ CFU/ml. Samples M02526, M02527, M02528 are water exiting the experimental system described above after the operation of thickness sterilization system as described in FIG. 4. The bacteria count of these samples was $8.7 \times 10^4$, $7.0 \times 10^4$, and $5.1 \times 10^4$ CFU/ml respectively. Sample MO2525 is water exiting the experimental system described above after the operation of the longitudinal sterilization system as described in FIG. 11. The bacteria count of this sample was $1.3 \times 10^3$ CFU/ml. Sample M02529 is water exiting the experimental system described above after the operation of the torsion sterilization system as described in FIG. 21. The bacteria count of this sample was <100 CFU/ml. For the samples exiting the thickness sterilization system no significant reduction of the bacteria count was achieved. For sample MO2525 exiting the longitudinal sterilization system a reduction of approximately 2 orders of magnitude was achieved in the bacteria count. For sample MO2529 exiting the torsion sterilization system where thickness, longitude and torsion vibrations were applied a reduction of more them 3 orders of magnitude was achieved in the bacteria count.

A second microbial test that includes a bacteria count and a mold count was conducted by MicroLab Laboratories, Rehovot, an officially recognized laboratory by Ministry of Agriculture, in Israel. The bacteria used were ERWINIA and CLAVIBACTER and the mold were ASPERILLUS and FUSARIUM. The Laboratory method was conducted according to the "Standard Methods for the Examination of Water and Wastewater" using the pour plate technique.

FIG. 32 illustrates the experimental results for the experimental system and method-described above, as accepted from the MicroLab Laboratories.

Six samples 1-6 were detected. Sample 6 is the control sample contains untreated examined water with initial bacterial count of $4 \times 10^8$ CFU/ml and mold count of $4.2 \times 10^5$ CFU/ml. Samples 3 and 4 are water exiting the experimental system described above after the operation of thickness sterilization system. The bacteria count of these samples was $1.2 \times 10^7$, $1.2 \times 10^8$ CFU/ml respectively and the mold count was <10 and $3 \times 10^4$ CFU/ml respectively. Samples 2 and 1 are water exiting the experimental system described above after the operation of longitudinal sterilization system, where the longitude mode is at the first and second mode as described in FIGS. 12A and 12B respectively. The bacteria count of these samples was $4.1 \times 10^6$ and $8.6 \times 10^3$ CFU/ml for the first and second mode and the mold count for both modes was <10 CFU/ml. Sample 5 is water exiting the experimental system described above after the operation of torsion sterilization system. The bacteria and mold count of this sample were <10 CFU/ml.

For the samples exiting the thickness sterilization system no significant reduction of the bacteria count was achieved. For sample 2 and 1 exiting the longitudinal sterilization system where longitude vibrations were applied at the first and second mode of vibration a reduction of approximately 2 and 5 orders of magnitude was achieved in the bacteria count, respectively. For both samples the mold count was reduced to <10 CFU/ml. For sample 5 exiting the torsion sterilization system a reduction of 8 orders of magnitude was achieved in the bacteria count and the mold count was reduced to <10 CFU/ml.

The most efficient sterilization system as accepted at both laboratories is the system described in FIG. 21 where a combination of thickness, longitude and torsion vibrations are applied.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An apparatus to substantially sterilize a liquid comprising:
    at least one ring of piezoceramic material, the ring being of an arbitrary shape and length, and being attached to the inner side of a sterilization tube, which has an internal passage with non-flowing or flowing liquid; and
    a power supply system connected to the ring and adapted to supply electric waves to the ring at a frequency estimated to be a resonance frequency of a system formed by the ring and the liquid; thereby focusing acoustic standing waves, wherein a high pressure and a cavitation column is produced in the middle of the ring.

2. The apparatus of claim 1, wherein the ring has dimensions of 0.05-50 mm thickness; 1-100 mm inner radius; and 1-1000 mm length; and a shape selected from the group consisting of cylindrical, convex, concave, and tapered.

3. The apparatus of claim 2, wherein said ring is coated on at least one surface by a conducting material, the conducting material being selected from a group consisting of: silver, gold, nickel, and conducting rubber.

4. The apparatus of claim 3, wherein said electric waves cause said ring to vibrate along its thickness.

5. The apparatus of claim 4, wherein the electric waves cause the ring to vibrate such that standing thickness waves are produced within the liquid.

6. The apparatus of claim 3, wherein said electric waves cause said ring to produce torsion vibrations.

7. The apparatus of claim 6, wherein the electric waves cause said ring to vibrate such that standing torsion waves are produced within the liquid.

8. The apparatus of claim 3, wherein said electric waves cause said ring to vibrate along its length.

9. The apparatus of claim 8, wherein the electric waves cause the ring to produce standing longitudinal waves within the liquid.

10. The apparatus of claim 3 wherein the power supply system comprises a pulse power supplier, a MHz power supplier, an amplifier, a controller, and a sensing device, wherein the MHz power supplier is to produce electric waves in the frequency range of 0.1-20 MHz.

11. The apparatus of claim 10 wherein the electric waves are in the range of 0.1-20MHz and cause thickness and torsion vibration modes in the ring.

12. The apparatus of claim 3 wherein the power supply system further comprises a KHz power supplier, for producing electric waves in the range of 20-500KHz, and exciting the 1st or 2nd vibration modes.

13. The apparatus of claim 12, further comprising a mixer to mix electric waves intended to produce thickness, torsion and longitudinal vibratiojns.

14. The apparatus of claim 2 comprising: a second piezoceramic ring, wherein the first and the second ring are constructed from the same or different piezo material, wherein the ring dimensions, shape and materials resulting in variable shapes of cavitation area along the ring.

15. A device to substantially sterilize a liquid comprising:
a piezoceramic ring, said ring being of an arbitary shape and length, and being attached to an inner diameter of a tubular sterilization container, which has an internal passage with non-flowing or flowing liquid; and a power supply system connected to said ring and adapted to supply electric waves to said ring at a frequency estimated to be a resonance frequency of a system formed by said ring and the liquid; thereby focusing acoustic standing waves, wherein a cavitation column is produced in the middle of the ring.

* * * * *